(12) United States Patent
Villalobos et al.

(10) Patent No.: US 9,714,208 B2
(45) Date of Patent: *Jul. 25, 2017

(54) CATALYSTS CONVERSION OF HYDROXYPROPIONIC ACID OR ITS DERIVATIVES TO ACRYLIC ACID OR ITS DERIVATIVES

(71) Applicant: The Procter & Gamble Company, Cincinnati, OH (US)

(72) Inventors: Janette Villalobos, Cincinnati, OH (US); Juan Estaban Velasquez, Cincinnati, OH (US); Jane Ellen Godlewski, Loveland, OH (US); Dimitris Ioannis Collias, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 304 days.

This patent is subject to a terminal disclaimer.

(21) Appl. No.: 13/760,472

(22) Filed: Feb. 6, 2013

(65) Prior Publication Data

US 2013/0274512 A1    Oct. 17, 2013

Related U.S. Application Data

(60) Provisional application No. 61/623,054, filed on Apr. 11, 2012.

(51) Int. Cl.

| C07C 51/377 | (2006.01) |
|---|---|
| C07C 51/48 | (2006.01) |
| B01J 27/18 | (2006.01) |
| B01J 27/187 | (2006.01) |
| B01J 27/25 | (2006.01) |
| C07C 51/09 | (2006.01) |
| C07C 57/04 | (2006.01) |
| A61F 13/534 | (2006.01) |
| C08F 2/10 | (2006.01) |
| B01J 27/16 | (2006.01) |
| B01J 27/185 | (2006.01) |
| B01J 27/186 | (2006.01) |
| B01J 27/188 | (2006.01) |
| B01J 27/195 | (2006.01) |
| B01J 27/198 | (2006.01) |
| B01J 35/02 | (2006.01) |
| B01J 37/00 | (2006.01) |
| B01J 37/04 | (2006.01) |
| B01J 37/08 | (2006.01) |
| C07C 51/44 | (2006.01) |
| A61F 13/53 | (2006.01) |

(52) U.S. Cl.

CPC ............ *C07C 51/48* (2013.01); *A61F 13/534* (2013.01); *B01J 27/16* (2013.01); *B01J 27/1806* (2013.01); *B01J 27/186* (2013.01); *B01J 27/187* (2013.01); *B01J 27/188* (2013.01); *B01J 27/1811* (2013.01); *B01J 27/1817* (2013.01); *B01J 27/1853* (2013.01); *B01J 27/1856* (2013.01); *B01J 27/195* (2013.01); *B01J 27/198* (2013.01); *B01J 27/25* (2013.01); *B01J 35/023* (2013.01); *B01J 37/0036* (2013.01); *B01J 37/04* (2013.01); *B01J 37/08* (2013.01); *C07C 51/09* (2013.01); *C07C 51/377* (2013.01); *C07C 51/44* (2013.01); *C07C 57/04* (2013.01); *C08F 2/10* (2013.01); *A61F 13/53* (2013.01); *A61F 2013/530489* (2013.01); *A61F 2013/530496* (2013.01)

(58) Field of Classification Search
None
See application file for complete search history.

(56) References Cited

U.S. PATENT DOCUMENTS

| 2,859,240 | A | * | 11/1958 | Holmen ........................ 560/212 |
|---|---|---|---|---|
| 3,781,222 | A | | 12/1973 | Weisang et al. |
| 4,695,661 | A | | 9/1987 | Homann et al. |
| 4,729,978 | A | | 3/1988 | Sawicki |
| 4,786,756 | A | | 11/1988 | Paparizos et al. |
| 5,071,754 | A | * | 12/1991 | Walkup et al. ............... 435/135 |
| 7,683,220 | B2 | | 3/2010 | Matsunami et al. |

FOREIGN PATENT DOCUMENTS

| CN | 200910054519.7 | | 7/2009 |
|---|---|---|---|
| CN | 101537362 | * | 9/2009 |
| GB | 1489832 | | 10/1977 |
| WO | WO 03/082795 | | 10/2003 |

OTHER PUBLICATIONS

Kirk-Othmer Encyclopedia of Chemical Technology, David R. Gard, Published Online: Jul. 15, 2005, Copyright © 2001 John Wiley & Sons, pp. 1-56.*
Machine translation of CN 101537362 availible at http://worldwide.espacenet.com/.*
Machine translation of CN 101537362 (2009) availible at http://worldwide.espacenet.com/.*
Gunter et al.; J. Catalysis 148:252-260, 1994.
Hong et al.; Appl. Catal. A: General 396:194-200, 2011.
Kirk-Othmer Encylcopedia of Chemical Technology, vol. 1, pp. 324-369, 5th Ed., John Wiley & Sons, Inc., 2004.
Tam et al.; Ind. Eng. Chem. Res: 38:3873-3877, 1999.
International Search Report and Written Opinion for 12735 dated Sep. 6, 2013.

* cited by examiner

*Primary Examiner* — Karl J Puttlitz
(74) *Attorney, Agent, or Firm* — Brent M. Peebles

(57) ABSTRACT

Methods for catalytically dehydrating hydroxypropionic acid, hydroxypropionic acid derivatives, or mixtures thereof to acrylic acid, acrylic acid derivatives, or mixtures thereof with high yield and selectivity and without significant conversion to undesired side products, such as, acetaldehyde, propionic acid, and acetic acid, are provided. The catalysts are mixed condensed phosphates.

29 Claims, No Drawings

CATALYSTS CONVERSION OF HYDROXYPROPIONIC ACID OR ITS DERIVATIVES TO ACRYLIC ACID OR ITS DERIVATIVES

FIELD OF THE INVENTION

The present invention generally relates to methods of catalytic conversion of hydroxypropionic acid, hydroxypropionic acid derivatives, or mixtures thereof to acrylic acid, acrylic acid derivatives, or mixtures thereof. More specifically, the invention relates to methods of using catalysts useful for the dehydration of hydroxypropionic acid, hydroxypropionic acid derivatives, or mixtures thereof to acrylic acid, acrylic acid derivatives, or mixtures thereof with high yield and selectivity to acrylic acid, acrylic acid derivatives, or mixtures thereof, short residence time, and without significant conversion of the hydroxypropionic acid, hydroxypropionic acid derivatives, or mixtures thereof to undesired side products, such as, for example, acetaldehyde, propionic acid, acetic acid, 2,3-pentanedione, carbon dioxide, and carbon monoxide.

BACKGROUND OF THE INVENTION

Acrylic acid, acrylic acid derivatives, or mixtures thereof have a variety of industrial uses, typically consumed in the form of polymers. In turn, these polymers are commonly used in the manufacture of, among other things, adhesives, binders, coatings, paints, polishes, detergents, flocculants, dispersants, thixotropic agents, sequestrants, and superabsorbent polymers, which are used in disposable absorbent articles, including diapers and hygienic products, for example. Acrylic acid is commonly made from petroleum sources. For example, acrylic acid has long been prepared by catalytic oxidation of propylene. These and other methods of making acrylic acid from petroleum sources are described in the Kirk-Othmer Encyclopedia of Chemical Technology, Vol. 1, pgs. 342-369 ($5^{th}$ Ed., John Wiley & Sons, Inc., 2004). Petroleum-based acrylic acid contributes to greenhouse emissions due to its high petroleum derived carbon content. Furthermore, petroleum is a non-renewable material, as it takes hundreds of thousands of years to form naturally and only a short time to consume. As petrochemical resources become increasingly scarce, more expensive, and subject to regulations for $CO_2$ emissions, there exists a growing need for bio-based acrylic acid, acrylic acid derivatives, or mixtures thereof that can serve as an alternative to petroleum-based acrylic acid, acrylic acid derivatives, or mixtures thereof.

Many attempts have been made over the last 40 to 50 years to make bio-based acrylic acid, acrylic acid derivatives, or mixtures thereof from non-petroleum sources, such as lactic acid (also known as 2-hydroxypropionic acid), 3-hydroxypropionic acid, glycerin, carbon monoxide and ethylene oxide, carbon dioxide and ethylene, and crotonic acid. From these non-petroleum sources, only lactic acid is produced today in high yield from sugar (≥90% of theoretical yield, or equivalently, ≥0.9 g of lactic acid per g of sugar) and purity, and economics which could support producing acrylic acid at a cost competitive to petroleum-based acrylic acid. As such, lactic acid or lactate presents a real opportunity of serving as a feedstock for bio-based acrylic acid, acrylic acid derivatives, or mixtures thereof. Also, 3-hydroxypropionic acid is expected to be produced at commercial scale in a few years, and as such, 3-hydropropionic acid will present another real opportunity of serving as feedstock for bio-based acrylic acid, acrylic acid derivatives, or mixtures thereof. Sulfate salts; phosphate salts; mixtures of sulfate and phosphate salts; bases; zeolites or modified zeolites; metal oxides or modified metal oxides; and supercritical water are the main catalysts which have been used to dehydrate lactic acid or lactate to acrylic acid, acrylic acid derivatives, or mixtures thereof in the past with varying success.

For example, U.S. Pat. No. 4,786,756 (issued in 1988), describes the vapor phase dehydration of lactic acid or ammonium lactate to acrylic acid using aluminum phosphate ($AlPO_4$) treated with an aqueous inorganic base as a catalyst. As an example, the '756 patent discloses a maximum yield of acrylic acid of 43.3% when lactic acid was fed into the reactor at approximately atmospheric pressure, and a respective yield of 61.1% when ammonium lactate was fed into the reactor. In both examples, acetaldehyde was produced at yields of 34.7% and 11.9%, respectively, and other side products were also present in large quantities, such as, propionic acid, CO, and $CO_2$. Omission of the base treatment caused increased amounts of the side products. Another example is Hong et al. (2011) *Appl. Catal. A: General* 396:194-200, who developed and tested composite catalysts made with $Ca_3(PO_4)_2$ and $Ca_2(P_2O_7)$ salts with a slurry-mixing method. The catalyst with the highest yield of acrylic acid from methyl lactate was the 50%-50% (by weight) catalyst. It yielded 68% acrylic acid, about 5% methyl acrylate, and about 14% acetaldehyde at 390° C. The same catalyst achieved 54% yield of acrylic acid, 14% yield of acetaldehyde, and 14% yield of propionic acid from lactic acid.

Prof. D. Miller's group at Michigan State University (MSU) published many papers on the dehydration of lactic acid or lactic acid esters to acrylic acid and 2,3-pentanedione, such as, Gunter et al. (1994) *J. Catalysis* 148: 252-260; and Tam et al. (1999) *Ind. Eng. Chem. Res.* 38:3873-3877. The best acrylic acid yields reported by the group were about 33% when lactic acid was dehydrated at 350° C. over low surface area and pore volume silica impregnated with NaOH. In the same experiment, the acetaldehyde yield was 14.7% and the propionic acid yield was 4.1%. Examples of other catalysts tested by the group were $Na_2SO_4$, NaCl, $Na_3PO_4$, $NaNO_3$, $Na_2SiO_3$, $Na_4P_2O_7$, $NaH_2PO_4$, $Na_2HPO_4$, $Na_2HAsO_4$, $NaC_3H_5O_3$, NaOH, CsCl, $Cs_2SO_4$, KOH, CsOH, and LiOH. In all cases, the above referenced catalysts were tested as individual components, not in mixtures. Finally, the group suggested that the yield to acrylic acid is improved and the yield to the side products is suppressed when the surface area of the silica support is low, reaction temperature is high, reaction pressure is low, and residence time of the reactants in the catalyst bed is short.

Finally, the Chinese patent application 200910054519.7 discloses the use of ZSM-5 molecular sieves modified with aqueous alkali (such as, $NH_3$, NaOH, and $Na_2CO_3$) or a phosphoric acid salt (such as, $NaH_2PO_4$, $Na_2HPO_4$, $LiH_2PO_4$, $LaPO_4$, etc.). The best yield of acrylic acid achieved in the dehydration of lactic acid was 83.9%, however that yield came at very long residence times.

Therefore, the manufacture of acrylic acid, acrylic acid derivatives, or mixtures thereof from lactic acid or lactate by processes, such as those described in the literature noted above, has demonstrated: 1) yields of acrylic acid, acrylic acid derivatives, or mixtures thereof not exceeding 70%; 2) low selectivities of acrylic acid, acrylic acid derivatives, or mixtures thereof, i.e., significant amounts of undesired side products, such as, acetaldehyde, 2,3-pentanedione, propionic acid, CO, and CO$_2$; 3) long residence times in the catalyst beds; and 4) catalyst deactivation in short time on stream (TOS). The side products can deposit onto the catalyst resulting in fouling, and premature and rapid deactivation of the catalyst. Further, once deposited, these side products can catalyze other undesired reactions, such as polymerization reactions. Aside from depositing on the catalysts, these side products, even when present in only small amounts, impose additional costs in processing acrylic acid (when present in the reaction product effluent) in the manufacture of superabsorbent polymers (SAP), for example. These deficiencies of the prior art processes and catalysts render them commercially non-viable.

Accordingly, there is a need for catalysts and methods for the dehydration of hydroxypropionic acid, hydroxypropionic acid derivatives, or mixtures thereof to acrylic acid, acrylic acid derivatives, or mixtures thereof, with high yield, selectivity, and efficiency (i.e., short residence time), and high longevity catalysts.

SUMMARY OF THE INVENTION

A method of making acrylic acid, acrylic acid derivatives, or mixtures thereof is provided. In one embodiment, the method includes contacting a stream comprising hydroxypropionic acid, hydroxypropionic acid derivatives, or mixtures thereof with a catalyst comprising: (a) at least one condensed phosphate anion selected from the group consisting of formulae (I), (II), and (III), $$[P_nO_{3n+1}]^{(n+2)-} \qquad (I)$$

$$[P_nO_{3n}]^{n-} \qquad (II)$$

$$[P_{(2m+n)}O_{(5m+3n)}]^{n-} \qquad (III)$$

wherein n is at least 2 and m is at least 1, and (b) at least two different cations, wherein the catalyst is essentially neutrally charged, and further, wherein the molar ratio of phosphorus to the at least two different cations is between about 0.7 and about 1.7, whereby acrylic acid, acrylic acid derivatives, or mixtures thereof are produced as a result of said stream being contacted with said catalyst. The anions defined by formulae (I), (II), and (III) are also referred to as polyphosphates (or oligophosphates), cyclophosphates, and ultraphosphates, respectively.

In one embodiment of the present invention, a method of making acrylic acid includes contacting: (a) a gaseous stream comprising: (i) lactic acid, (ii) water, and (iii) nitrogen, wherein said lactic acid is present in an amount of about 2.5 mol % and wherein said water is present in an amount of about 50 mol % based on the total moles of said gaseous stream, with (b) a catalyst comprising (i) $Ba_{2-x-s}K_{2x}H_{2s}P_2O_7$, and (ii) $(KPO_3)_n$, wherein x and s are greater or equal to 0 and less than about 0.5 and n is a positive integer, wherein, said contacting of said gaseous stream with said catalyst is performed at a temperature of about 300° C. to about 450° C., at a Gas Hourly Space Velocity (GHSV) of about 3,600 h$^{-1}$ and at a pressure of about 360 psig, in a reactor having an interior surface comprising material selected from the group consisting of quartz and borosilicate glass, whereby acrylic acid is produced as a result of said lactic acid being contacted with said catalyst.

In another embodiment of the present invention, a method of making acrylic acid includes contacting: (a) a gaseous stream comprising: (i) lactic acid, (ii) water, and (iii) nitrogen, wherein said lactic acid is present in an amount of about 2.5 mol % and wherein said water is present in an amount of 50 mol % based on the total moles of said gaseous stream, with (b) a catalyst prepared by a method comprising the following steps: (i) combining a phosphorus containing compound, a nitrate salt, phosphoric acid, and water to form a wet mixture, wherein the molar ratio between phosphorus and the cations in both said phosphorus containing compound and said nitrate salt is about 1; (ii) calcining said wet mixture stepwise at about 50° C., about 80° C., about 120° C., and about 450° C. to about 550° C. to produce a dried solid; and (iii) grinding and sieving said dried solid to about 100 μm to about 200 μm, to produce said catalyst, and wherein, said contacting of said gaseous stream with said catalyst is performed at a temperature of about 300° C. to about 450° C., at a GHSV of about 3,600 h$^{-1}$ and at a pressure of about 360 psig, in a reactor having an interior surface comprising material selected from the group consisting of quartz and borosilicate glass, whereby acrylic acid is produced as a result of said lactic acid being contacted with said catalyst.

In yet another embodiment of the present invention, a method of making acrylic acid includes contacting: (a) a gaseous stream comprising: (i) lactic acid, (ii) water, and (iii) nitrogen, wherein said lactic acid is present in an amount of about 2.5 mol % and wherein said water is present in an amount of about 50 mol % based on the total moles of said gaseous stream, with (b) a catalyst prepared by a method comprising the following steps: (i) combining $Ca_2P_2O_7$ and $KH_2PO_4$ in a molar ratio of about 3:1 to form a solid mixture; and (ii) calcining said solid mixture stepwise at about 50° C., about 80° C., about 120° C., and about 450° C. to about 550° C., to produce said catalyst; and wherein, said contacting of said gaseous stream with said catalyst is performed at a temperature of about 300° C. to about 450° C., at a GHSV of about 3,600 h$^{-1}$ and at a pressure of about 360 psig, in a reactor having an interior surface comprising material selected from the group consisting of quartz and borosilicate glass, whereby acrylic acid is produced as a result of said lactic acid being contacted with said catalyst.

Additional features of the invention may become apparent to those skilled in the art from a review of the following detailed description, taken in conjunction with the examples.

DETAILED DESCRIPTION OF THE INVENTION

I Definitions

As used herein, the term "monophosphate" or "orthophosphate" refers to any salt whose anionic entity, $[PO_4]^{3-}$, is composed of four oxygen atoms arranged in an almost regular tetrahedral array about a central phosphorus atom.

As used herein, the term "condensed phosphate" refers to any salts containing one or several P—O—P bonds generated by corner sharing of PO$_4$ tetrahedra.

As used herein, the term "polyphosphate" refers to any condensed phosphates containing linear P—O—P linkages by corner sharing of PO$_4$ tetrahedra leading to the formation of finite chains.

As used herein, the term "oligophosphate" refers to any polyphosphates that contain five or less PO$_4$ units.

As used herein, the term "cyclophosphate" refers to any cyclic condensed phosphate constituted of two or more corner-sharing PO$_4$ tetrahedra.

As used herein, the term "ultraphosphate" refers to any condensed phosphate where at least two PO$_4$ tetrahedra of the anionic entity share three of their corners with the adjacent ones.

As used herein, the term "cation" refers to any atom or group of covalently-bonded atoms having a positive charge.

As used herein, the term "anion" refers to any atom or group of covalently-bonded atoms having a negative charge.

As used herein, the term "monovalent cation" refers to any cation with a positive charge of +1.

As used herein, the term "polyvalent cation" refers to any cation with a positive charge equal or greater than +2.

As used herein, the term "heteropolyanion" refers to any anion with covalently bonded XO$_p$ and YO$_r$ polyhedra, and thus includes X—O—Y and possibly X—O—X and Y—O—Y bonds, wherein X and Y represent any atoms, and wherein p and r are any positive integers.

As used herein, the term "heteropolyphosphate" refers to any heteropolyanion, wherein X represents phosphorus (P) and Y represents any other atom.

As used herein, the term "phosphate adduct" refers to any compound with one or more phosphate anions and one or more non-phosphate anions that are not covalently linked.

As used herein, the terms "LA" refers to lactic acid, "AA" refers to acrylic acid, "AcH" refers to acetaldehyde, and "PA" refers to propionic acid.

As used herein, the term "particle span" refers to a statistical representation of a given particle sample and is equal to $(D_{v,0.90}-D_{v,0.10})/D_{v,0.50}$. The term "median particle size" or $D_{v,0.50}$ refers to the diameter of a particle below which 50% of the total volume of particles lies. Further, $D_{v,0.10}$ refers to the particle size that separates the particle sample at the 10% by volume fraction and $D_{v,0.90}$, is the particle size that separates the particle sample at the 90% by volume fraction.

As used herein, the term "conversion" in % is defined as [hydroxypropionic acid, hydroxypropionic acid derivatives, or mixtures thereof flow rate in (mol/min)–hydroxypropionic acid, hydroxypropionic acid derivatives, or mixtures thereof flow rate out (mol/min)]/[hydroxypropionic acid, hydroxypropionic acid derivatives, or mixtures thereof flow rate in (mol/min)]*100. For the purposes of this invention, the term "conversion" means molar conversion, unless otherwise noted.

As used herein, the term "yield" in % is defined as [product flow rate out (mol/min)/hydroxypropionic acid, hydroxypropionic acid derivatives, or mixtures thereof flow rate in (mol/min)]*100. For the purposes of this invention, the term "yield" means molar yield, unless otherwise noted.

As used herein, the term "selectivity" in % is defined as [Yield/Conversion]*100. For the purposes of this invention, the term "selectivity" means molar selectivity, unless otherwise noted.

As used herein, the term "total flow rate out" in mol/min and for hydroxypropionic acid is defined as: (2/3)*[C2 flow rate out (mol/min)]+[C3 flow rate out (mol/min)]+(2/3)*[acetaldehyde flow rate out (mol/min)]+(4/3)*[C4 flow rate out (mol/min)]+[hydroxypropionic acid flow rate out (mol/min)]+[pyruvic acid flow rate out (mol/min)]+(2/3)*[acetic acid flow rate out (mol/min)]+[1,2-propanediol flow rate out (mol/min)]+[propionic acid flow rate out (mol/min)]+[acrylic acid flow rate out (mol/min)]+(5/3)*[2,3-pentanedione flow rate out (mol/min)]+(1/3)*[carbon monoxide flow rate out (mol/min)]+(1/3)*[carbon dioxide flow rate out (mol/min)]. If a hydroxypropionic acid derivative is used instead of hydroxypropionic acid, the above formula needs to be adjusted according to the number of carbon atoms in the hydroxypropionic acid derivative.

As used herein, the term "C2" means ethane and ethylene.

As used herein, the term "C3" means propane and propylene.

As used herein, the term "C4" means butane and butenes.

As used herein, the term "total molar balance" or "TMB" in % is defined as [total flow rate out (mol/min)/hydroxypropionic acid, hydroxypropionic acid derivatives, or mixtures thereof flow rate in (mol/min)]*100.

As used herein, the term "the acrylic acid yield was corrected for TMB" is defined as [acrylic acid yield/total molar balance]*100, to account for slightly higher flows in the reactor.

As used herein, the term "Gas Hourly Space Velocity" or "GHSV" in h$^{-1}$ is defined as [Total gas flow rate (mL/min)/catalyst bed volume (mL)]/60. The total gas flow rate is calculated under Standard Temperature and Pressure conditions (STP; 0° C. and 1 atm).

As used herein, the term "Liquid Hourly Space Velocity" or "LHSV" in h$^{-1}$ is defined as [Total liquid flow rate (mL/min)/catalyst bed volume (mL)]/60.

II Catalysts

Unexpectedly, it has been found that mixed condensed phosphate catalysts dehydrate hydroxypropionic acid, hydroxypropionic acid derivatives, or mixtures thereof to acrylic acid, acrylic acid derivatives, or mixtures thereof with high: 1) yield and selectivity for acrylic acid, acrylic acid derivatives, or mixtures thereof, i.e., low amount and few side products; 2) efficiency, i.e., performance in short residence time; and 3) longevity. Although not wishing to be bound by any theory, applicants hypothesize that the catalyst, which includes at least one condensed phosphate anion and two different cations, works as follows: the carboxylate group of the hydroxypropionic acid, hydroxypropionic acid derivatives, or mixtures thereof, associates with one or several cations, which in one embodiment is polyvalent, through one or both oxygen atoms, holding the molecule onto the surface of the catalyst, deactivating it from decarbonylation, and activating the C—OH bond for elimination. Then, the resulting protonated condensed phosphate anion dehydrates the hydroxypropionic acid, hydroxypropionic acid derivatives, or mixtures thereof by concerted protonation of the hydroxyl group, removal of a proton from the methyl group, and elimination of the protonated hydroxyl group as a molecule of water, generating acrylic acid, acrylic acid derivatives, or mixtures thereof and reactivating the catalyst. Furthermore, applicants believe that when the hydroxypropionic acid, hydroxypropionic acid derivatives, or mixtures thereof are diluted with water, some condensed phosphate salts in the catalyst can be hydrolyzed to uncondensed monophosphates or shorter condensed phosphates, which can be transformed into a liquid state under the proper temperature and pressure conditions, facilitating the dehydration of hydroxypropionic acid, hydroxypropionic acid derivatives, or mixtures thereof.

In one embodiment, the catalyst comprises: (a) at least one condensed phosphate anion selected from the group consisting of formulae (I), (II), and (III),

wherein n is at least 2 and m is at least 1, and (b) at least two different cations, wherein the catalyst is essentially neutrally charged, and further, wherein the molar ratio of phosphorus to the at least two different cations is between about 0.7 and about 1.7.

The anions defined by formulae (I), (II), and (III) are also referred to as polyphosphates (or oligophosphates), cyclophosphates, and ultraphosphates, respectively.

In another embodiment, the catalyst comprises: (a) at least one condensed phosphate anion selected from the group consisting of formulae (I) and (II),

     (I)

     (II)

wherein n is at least 2, and (b) at least two different cations, wherein the catalyst is essentially neutrally charged, and further, wherein the molar ratio of phosphorus to the at least two different cations is between about 0.7 and about 1.7.

The cations can be monovalent or polyvalent. In one embodiment, one cation is monovalent and the other cation is polyvalent. In another embodiment, the polyvalent cation is selected from the group consisting of divalent cations, trivalent cations, tetravalent cations, pentavalent cations, and mixtures thereof. Non-limiting examples of monovalent cations are $H^+$, $Li^+$, $Na^+$, $K^+$, $Rb^+$, $Cs^+$, $Ag^+$, $Rb^+$, $Tl^+$, and mixtures thereof. In one embodiment, the monovalent cation is selected from the group consisting of $Li^+$, $Na^+$, $K^+$, $Rb^+$, $Cs^+$, and mixtures thereof; in another embodiment, the monovalent cation is $Na^+$ or $K^+$; and in yet another embodiment, the monovalent cation is $K^+$. Non-limiting examples of polyvalent cations are cations of the alkaline earth metals (i.e., Be, Mg, Ca, Sr, Ba, and Ra), transition metals (e.g. Y, Ti, Zr, V, Nb, Cr, Mo, Mn, Re, Fe, Ru, Co, Rh, Ni, Pd, Pt, Cu, Ag, and Au), poor metals (e.g. Zn, Ga, Si, Ge, B, Al, In, Sb, Sn, Bi, and Pb), lanthanides (e.g. La and Ce), and actinides (e.g. Ac and Th). In one embodiment, the polyvalent cation is selected from the group consisting of $Be^{2+}$, $Mg^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, $Zn^{2+}$, $Cd^{2+}$, $Sn^{2+}$, $Pb^{2+}$, $Ti^{3+}$, $Cr^{3+}$, $Mn^{3+}$, $Fe^{3+}$, $Al^{3+}$, $Ga^{3+}$, $Y^{3+}$, $In^{3+}$, $Sb^{3+}$, $Bi^{3+}$, $Si^{4+}$, $Ti^{4+}$, $V^{4+}$, $Ge^{4+}$, $Mo^{4+}$, $Pt^{4+}$, $V^{5+}$, $Nb^{5+}$, $Sb^{5+}$, and mixtures thereof. In one embodiment, the polyvalent cation is selected from the group consisting of $Ca^{2+}$, $Ba^{2+}$, $Cu^{2+}$, $Mn^{2+}$, $Mn^{3+}$, and mixtures thereof; in another embodiment, the polyvalent cation is selected from the group consisting of $Ca^{2+}$, $Ba^{2+}$, $Mn^{3+}$, and mixtures thereof; and in yet another embodiment, the polyvalent cation is $Ba^{2+}$.

The catalyst can include cations: (a) $H^+$, $Li^+$, $Na^+$, $K^+$, $Rb^+$, $Cs^+$, or mixtures thereof; and (b) $Be^{2+}$, $Mg^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, $Zn^{2+}$, $Cd^{2+}$, $Sn^{2+}$, $Pb^{2+}$, $Ti^{3+}$, $Cr^{3+}$, $Mn^{3+}$, $Fe^{3+}$, $Al^{3+}$, $Ga^{3+}$, $Y^{3+}$, $In^{3+}$, $Sb^{3+}$, $Bi^{3+}$, $Si^{4+}$, $Ti^{4+}$, $V^{4+}$, $Ge^{4+}$, $Mo^{4+}$, $Pt^{4+}$, $V^{5+}$, $Nb^{5+}$, $Sb^{5+}$, or mixtures thereof. In one embodiment the catalyst comprises $Li^+$, $Na^+$, or $K^+$ as monovalent cation, and $Ca^{2+}$, $Ba^{2+}$, or $Mn^{3+}$ as polyvalent cation; in another embodiment, the catalyst comprises $Na^+$ or $K^+$ as monovalent cation, and $Ca^{2+}$ or $Ba^{2+}$ as polyvalent cation; and in yet another embodiment, the catalyst comprises $K^+$ as the monovalent cation and $Ba^{2+}$ as the polyvalent cation.

In one embodiment, the catalyst comprises $Ba_{2-x-s}K_{2x}H_{2s}P_2O_7$ and $(KPO_3)$, wherein x and s are greater or equal to 0 and less than about 0.5 and n is a positive integer. In another embodiment, the catalyst comprises $Ca_{2-x-s}K_{2x}H_{2s}P_2O_7$ and $(KPO_3)$, wherein x and s are greater or equal to 0 and less than about 0.5 and n is a positive integer. In yet another embodiment, the catalyst comprises $Mn_{1-x-s}K_{1+3x}H_{3s}P_2O_7$ or $Mn_{1-x-s}K_{2+2x}H_{2s}P_2O_7$ and $(KPO_3)$ wherein x and s are greater or equal to 0 and less than about 0.5 and n is a positive integer. In another embodiment, the catalyst comprises any blend of $Ba_{2-x-s}K_{2x}H_{2s}P_2O_7$, $Ca_{2-x-s}K_{2x}H_{2s}P_2O_7$, $Mn_{1-x-s}K_{1+3x}H_{3s}P_2O_7$ or $Mn_{1-x-s}K_{2+2x}H_{2s}P_2O_7$; and $(KPO_3)_n$, wherein x and s are greater or equal to 0 and less than about 0.5 and n is a positive integer.

In one embodiment, the molar ratio of phosphorus to the cations in the catalyst is between about 0.7 and about 1.7; in another embodiment, the molar ratio of phosphorus to the cations in the catalyst is between about 0.8 and about 1.3; and in yet another embodiment, the molar ratio of phosphorus to the cations in the catalyst is about 1.

In one embodiment, the catalyst comprises: (a) at least two different condensed phosphate anions selected from the group consisting of formulae (I), (II), and (III),

     (I)

     (II)

     (III)

wherein n is at least 2 and m is at least 1, and (b) one cation, wherein the catalyst is essentially neutrally charged, and further, wherein the molar ratio of phosphorus to the cation is between about 0.5 and about 4.0. In another embodiment, the molar ratio of phosphorus to the cation is between about t/2 and about t, wherein t is the charge of the cation.

The catalyst can include an inert support that is constructed of a material comprising silicates, aluminates, carbons, metal oxides, and mixtures thereof. Alternatively, the carrier is inert relative to the reaction mixture expected to contact the catalyst. In the context of the reactions expressly described herein, in one embodiment the carrier is a low surface area silica or zirconia. When present, the carrier represents an amount of about 5 wt % to about 98 wt %, based on the total weight of the catalyst. Generally, a catalyst that includes an inert support can be made by one of two exemplary methods: impregnation or co-precipitation. In the impregnation method, a suspension of the solid inert support is treated with a solution of a pre-catalyst, and the resulting material is then activated under conditions that will convert the pre-catalyst to a more active state. In the co-precipitation method, a homogenous solution of the catalyst ingredients is precipitated by the addition of additional ingredients.

III Catalyst Preparation Methods

In one embodiment, the method of preparing the catalyst includes mixing and heating at least two different phosphorus containing compounds, wherein each said compound is described by one of the formulae (IV) to (XXV), or any of the hydrated forms of said formulae:

     (IV)

     (V)

     (VI)

     (VII)

     (VIII)

     (IX)

     (X)

     (XI)

$$M^{III}M^{I}{}_{3}(PO_4)_2 \quad (XII)$$

$$M^{IV}{}_{2}M^{I}(PO_4)_3 \quad (XIII)$$

$$M^{I}{}_{z}H_{4-z}P_2O_7 \quad (XIV)$$

$$M^{II}{}_{v}H_{(4-2v)}P_2O_7 \quad (XV)$$

$$M^{IV}P_2O_7 \quad (XVI)$$

$$(NH_4)_zH_{4-z}P_2O_7 \quad (XVII)$$

$$M^{III}M^{I}P_2O_7 \quad (XVIII)$$

$$M^{I}H_w(PO_3)_{(1+w)} \quad (XIX)$$

$$M^{II}H_w(PO_3)_{(1+w)} \quad (XX)$$

$$M^{III}H_w(PO_3)_{(4+w)} \quad (XXI)$$

$$M^{IV}H_w(PO_3)_{(4+w)} \quad (XXII)$$

$$M^{II}{}_{g}M^{I}{}_{h}(PO_3)_i \quad (XXIII)$$

$$M^{III}{}_{j}M^{I}{}_{k}(PO_3)_l \quad (XXIV)$$

$$P_2O_5 \quad (XXV)$$

wherein $M^I$ is a monovalent cation; wherein $M^{II}$ is a divalent cation; wherein $M^{III}$ is a trivalent cation; wherein $M^{IV}$ is a tetravalent cation; wherein y is 0, 1, 2, or 3; wherein z is 0, 1, 2, 3, or 4; wherein v is 0, 1, or 2; wherein w is 0 or any positive integer; and wherein a, b, c, d, e, f, g, h, i, j, k, and l are any positive integers, such that the equations: $2a=b+3c$, $3d=e+3f$, $i=2g+h$, and $l=3j+k$ are satisfied.

In one embodiment, the catalyst is prepared by mixing and heating one or more phosphorus containing compounds of formula (IV), wherein y is equal to 1, and one or more phosphorus containing compounds of formula (V), wherein y is equal to 2. In another embodiment, the catalyst is prepared by mixing and heating $M^{I}H_2PO_4$ and $M^{II}HPO_4$. In one embodiment, $M^I$ is $K^+$ and $M^{II}$ is $Ca^{2+}$, i.e., the catalyst is prepared by mixing and heating $KH_2PO_4$ and $CaHPO_4$; or $M^I$ is K and $M^{II}$ is $Ba^{2+}$, i.e., the catalyst is prepared by mixing and heating $KH_2PO_4$ and $BaHPO_4$.

In one embodiment, the catalyst is prepared by mixing and heating one or more phosphorus containing compound of formula (IV), wherein y is equal to 1, one or more phosphorus containing compounds of formula (XV), wherein v is equal to 2. In another embodiment, the catalyst is prepared by mixing and heating $M^{I}H_2PO_4$ and $M^{II}{}_2P_2O_7$. In one embodiment, $M^I$ is $K^+$ and $M^{II}$ is $Ca^{2+}$, i.e., the catalyst is prepared by mixing and heating $KH_2PO_4$ and $Ca_2P_2O_7$; or $M^I$ is $K^+$ and $M^{II}$ is $Ba^{2+}$, i.e., the catalyst is prepared by mixing and heating $KH_2PO_4$ and $Ba_2P_2O_7$.

In another embodiment, the molar ratio of phosphorus to the cations in the catalyst is between about 0.7 and about 1.7; in yet another embodiment, the molar ratio of phosphorus to the cations in the catalyst is between about 0.8 and about 1.3; and in another embodiment, the molar ratio of phosphorus to the cations in the catalyst is about 1.

In another embodiment, the method of preparing the catalyst includes mixing and heating (a) at least one phosphorus containing compound, wherein each said compound is described by one of the formulae (IV) to (XXV), or any of the hydrated forms of said formulae:

$$M^{I}{}_{y}(H_{3-y}PO_4) \quad (IV)$$

$$M^{II}{}_{y}(H_{3-y}PO_4)_2 \quad (V)$$

$$M^{III}{}_{y}(H_{3-y}PO_4)_3 \quad (VI)$$

$$M^{IV}{}_{y}(H_{3-y}PO_4)_4 \quad (VII)$$

$$(NH_4)_y(H_{3-y}PO_4) \quad (VIII)$$

$$M^{II}{}_{a}(OH)_b(PO_4)_c \quad (IX)$$

$$M^{III}{}_{d}(OH)_e(PO_4)_f \quad (X)$$

$$M^{II}M^{I}PO_4 \quad (XI)$$

$$M^{III}M^{I}{}_{3}(PO_4)_2 \quad (XII)$$

$$M^{IV}{}_{2}M^{I}(PO_4)_3 \quad (XIII)$$

$$M^{I}{}_{z}H_{4-z}P_2O_7 \quad (XIV)$$

$$M^{II}{}_{v}H_{(4-2v)}P_2O_7 \quad (XV)$$

$$M^{IV}P_2O_7 \quad (XVI)$$

$$(NH_4)_zH_{4-z}P_2O_7 \quad (XVII)$$

$$M^{III}M^{I}P_2O_7 \quad (XVIII)$$

$$M^{I}H_w(PO_3)_{(1+w)} \quad (XIX)$$

$$M^{II}H_w(PO_3)_{(2+w)} \quad (XX)$$

$$M^{III}H_w(PO_3)_{(3+w)} \quad (XXI)$$

$$M^{IV}H_w(PO_3)_{(4+w)} \quad (XXII)$$

$$M^{II}{}_{g}M^{I}{}_{h}(PO_3)_i \quad (XXIII)$$

$$M^{III}{}_{j}M^{I}{}_{k}(PO_3)_l \quad (XXIV)$$

$$P_2O_5 \quad (XXV)$$

wherein y is 0, 1, 2, or 3; wherein z is 0, 1, 2, 3, or 4; wherein v is 0, 1, or 2; wherein w is 0 or any positive integer; and wherein a, b, c, d, e, f, g, h, i, j, k, and l are any positive integers, such that the equations: $2a=b+3c$, $3d=e+3f$, $i=2g+h$, and $l=3j+k$ are satisfied, and (b) at least one non-phosphorus containing compound selected from the group consisting of nitrate salts, carbonate salts, acetate salts, metal oxides, chloride salts, sulfate salts, and metal hydroxides, wherein each said compound is described by one of the formulae (XXVI) to (XL), or any of the hydrated forms of said formulae:

$$M^{I}NO_3 \quad (XXVI)$$

$$M^{II}(NO_3)_2 \quad (XXVII)$$

$$M^{III}(NO_3)_3 \quad (XXVIII)$$

$$M^{I}{}_2CO_3 \quad (XXIX)$$

$$M^{II}CO_3 \quad (XXX)$$

$$M^{III}{}_2(CO_3)_3 \quad (XXXI)$$

$$(CH_3COO)M^{I} \quad (XXXII)$$

$$(CH_3COO)_2M^{II} \quad (XXXIII)$$

$$(CH_3COO)_3M^{III} \quad (XXXIV)$$

$$(CH_3COO)_4M^{IV} \quad (XXXV)$$

$$M^{I}{}_2O \quad (XXXVI)$$

$M^{II}O$ (XXXVII)

$M^{III}_2O_3$ (XXXVIII)

$M^{IV}O_2$ (XXXIX)

$M^{I}Cl$ (XXXX)

$M^{II}Cl_2$ (XXXXI)

$M^{III}Cl_3$ (XXXXII)

$M^{IV}Cl_4$ (XXXXIII)

$M^{I}_2SO_4$ (XXXXIV)

$M^{II}SO_4$ (XXXXV)

$M^{III}_2(SO_4)_3$ (XXXXVI)

$M^{IV}(SO_4)_2$ (XXXXVII)

$M^{I}OH$ (XXXVIII)

$M^{II}(OH)_2$ (XXXIX)

$M^{III}(OH)_3$ (XL).

In another embodiment, the non-phosphorus containing compounds can be selected from the group consisting of carboxylic acid-derived salts, halide salts, metal acetylacetonates, and metal alkoxides.

In one embodiment of the present invention, the molar ratio of phosphorus to the cations in the catalyst is between about 0.7 and about 1.7; in another embodiment, the molar ratio of phosphorus to the cations in the catalyst is between about 0.8 and about 1.3; and in yet another embodiment, the molar ratio of phosphorus to the cations in the catalyst is about 1.

In another embodiment of the present invention, the catalyst is prepared by mixing and heating one or more phosphorus containing compounds of formulae (IV) to (XXV) or their hydrated forms, and one or more nitrate salts of formulae (XXVI) to (XXVIII) or their hydrated forms. In another embodiment of the present invention, the catalyst is prepared by mixing and heating one or more phosphorus containing compounds of formula (IV) and one or more nitrate salts of formula (XXVII). In a further embodiment of the present invention, the catalyst is prepared by mixing and heating a phosphorus containing compound of formula (IV) wherein y is equal to 2, a phosphorus containing compound of formula (IV) wherein y is equal to 0 (i.e., phosphoric acid), and a nitrate salt of formula (XXVII). In yet another embodiment of the present invention, the catalyst is prepared by mixing and heating $K_2HPO_4$, $H_3PO_4$, and $Ba(NO_3)_2$. In yet another embodiment, the catalyst is prepared by mixing and heating $K_2HPO_4$, $H_3PO_4$, and $Ca(NO_3)_2$.

In one embodiment of the present invention, the catalyst is prepared by mixing and heating one or more phosphorus containing compounds of formula (IV) and one or more nitrate salts of formula (XXVIII). In a further embodiment of the present invention, the catalyst is prepared by mixing and heating a phosphorus containing compound of formula (IV) wherein y is equal to 2, a phosphorus containing compound of formula (IV) wherein y is equal to 0 (i.e., phosphoric acid), and a nitrate salt of formula (XXVIII). In yet another embodiment of the present invention, the catalyst is prepared by mixing and heating $K_2HPO_4$, $H_3PO_4$, and $Mn(NO_3)_2.4H_2O$.

In one embodiment of the present invention, the catalyst is prepared by mixing and heating one or more phosphorus containing compounds of formula (V) and one or more nitrate salts of formula (XXVI). In another embodiment of the present invention, the catalyst is prepared by mixing and heating a phosphorus containing compound of formula (V) wherein y is equal to 2, a phosphorus containing compound of formula (V) wherein y is equal to 0 (i.e., phosphoric acid), and a nitrate salt of formula (XXVI). In yet another embodiment of the present invention, the catalyst is prepared by mixing and heating $BaHPO_4$, $H_3PO_4$, and $KNO_3$. In another embodiment, the catalyst is prepared by mixing and heating $CaHPO_4$, $H_3PO_4$, and $KNO_3$.

In one embodiment of this invention, the catalyst is prepared by mixing and heating one or more phosphorus containing compounds of formula (V), one or more phosphorus containing compounds of formula (XV), and one or more nitrate salts of formula (XXVI). In a further embodiment of this invention, the catalyst is prepared by mixing and heating a phosphorus containing compound of formula (V), wherein y is equal to 0 (i.e., phosphoric acid); a phosphorus containing compound of formula (XV), wherein v is equal to 2; and a nitrate salt of formula (XXVI). In another embodiment of the present invention, the catalyst is prepared by mixing and heating $H_3PO_4$, $Ca_2P_2O_7$, and $KNO_3$. In yet another embodiment, the catalyst is prepared by mixing and heating $H_3PO_4$, $Ba_2P_2O_7$, and $KNO_3$.

In another embodiment of this invention, the catalyst is prepared by mixing and heating one or more phosphorus containing compounds of formula (VI) and one or more nitrate salts of formula (XXVI). In another embodiment of this invention, the catalyst is prepared by mixing and heating a phosphorus containing compound of formula (VI), wherein y is equal to 3; a phosphorus containing compound of formula (VI), wherein y is equal to 0 (i.e., phosphoric acid); and a nitrate salt of formula (XXVI). In yet another embodiment of this invention, the catalyst is prepared by mixing and heating $MnPO_4.qH_2O$, $H_3PO_4$, and $KNO_3$.

In one embodiment of this invention, the catalyst is prepared by mixing and heating one or more phosphorus containing compounds of formula (IV), one or more phosphorus containing compounds of formula (IX), and one or more nitrate salts of formula (XXVII). In another embodiment of this invention, the catalyst is prepared by mixing and heating a phosphorus containing compound of formula (IV), wherein y is equal to 2; a phosphorus containing compound of formula (IV), wherein y is equal to 0 (i.e., phosphoric acid); a phosphorus containing compound of formula (IX), wherein a is equal to 2, b is equal to 1, and c is equal to 1; and a nitrate salt of formula (XXVII). In yet another embodiment of this invention, the catalyst is prepared by mixing and heating $K_2HPO_4$, $H_3PO_4$, $Cu_2(OH)PO_4$, and $Ba(NO_3)_2$.

In one embodiment of this invention, the catalyst is prepared by mixing and heating one or more phosphorus containing compounds of formula (V), one or more phosphorus containing compounds of formula (IX), and one or more nitrate salts of formula (XXVI). In another embodiment of this invention, the catalyst is prepared by mixing and heating a phosphorus containing compound of formula (V), wherein y is equal to 3; a phosphorus containing compound of formula (V), wherein y is equal to 0 (i.e., phosphoric acid); a phosphorus containing compound of formula (IX), wherein a is equal to 2, b is equal to 1, and c is equal to 1; and a nitrate salt of formula (XXVI). In yet another embodiment, the catalyst is prepared by mixing and heating $Ba_3(PO_4)_2$, $H_3PO_4$, $Cu_2(OH)PO_4$, and $KNO_3$.

In one embodiment of the present invention, the catalyst is prepared by mixing and heating one or more phosphorus containing compounds described by one of the formulae (IV) to (XXV) or any of the hydrated forms, and one or more carbonate salts described by one of the formulae (XXIX) to (XXXI) or any of the hydrated forms.

In one embodiment of the present invention, the catalyst is prepared by mixing and heating one or more phosphorus containing compounds described by one of the formulae (IV) to (XXV) or any of the hydrated forms, and one or more acetate salts described by one of the formulae (XXXII) to (XXXV), any other organic acid-derived salts, or any of the hydrated forms.

In one embodiment of the present invention, the catalyst is prepared by mixing and heating one or more phosphorus containing compounds described by one of the formulae (IV) to (XXV) or any of the hydrated forms, and one or more metal oxides described by one of the formulae (XXXVI) to (XXXIX) or any of the hydrated forms.

In one embodiment of the present invention, the catalyst is prepared by mixing and heating one or more phosphorus containing compounds described by one of the formulae (IV) to (XXV) or any of the hydrated forms, and one or more chloride salts described by one of the formulae (XXXX) to (XXXXIII), any other halide salts, or any of the hydrated forms.

In one embodiment of the present invention, the catalyst is prepared by mixing and heating one or more phosphorus containing compounds described by one of the formulae (IV) to (XXV) or any of the hydrated forms, and one or more sulfate salts described by one of the formulae (XXXXIV) to (XXXXVII) or any of the hydrated forms.

In one embodiment of the present invention, the catalyst is prepared by mixing and heating one or more phosphorus containing compounds described by one of the formulae (IV) to (XXV) or any of the hydrated forms, and one or more hydroxides described by one of the formulae (XXXXVIII) to (XL) or any of the hydrated forms.

In one embodiment of the present invention, the catalyst is prepared by mixing and heating one or more phosphorus containing compounds of formulae (IV) to (XXV), and two or more non-phosphorus containing compounds of formulae (XXVI) to (XL) or their hydrated forms.

In one embodiment, the molar ratio of phosphorus to the cations (i.e., $M^I + M^{II} + M^{III} + \ldots$) is between about 0.7 and about 1.7; in another embodiment, the molar ratio of phosphorus to the cations (i.e., $M^I + M^{II} + M^{III} + \ldots$) is between about 0.8 and about 1.3, and in yet another embodiment, the molar ratio of phosphorus to the cations (i.e., $M^I + M^{II} + M^{III} + \ldots$) is about 1. For example, in an embodiment when the catalyst includes potassium (IC) and barium ($Ba^{2+}$), the molar ratio between phosphorus and the metals (K+Ba) is between about 0.7 and about 1.7; and in another embodiment, the molar ratio between phosphorus and the metals ($K^+$ Ba) is about 1.

When the catalyst includes only two different cations, the molar ratio between cations is, in one embodiment, between about 1:50 and about 50:1; and in another embodiment, the molar ratio between cations is between about 1:4 and about 4:1. For example, when the catalyst includes potassium ($K^+$) and barium ($Ba^{2+}$), the molar ratio between them (K:Ba), in one embodiment, is between about 1:4 and about 4:1. Also, when the catalyst is prepared by mixing and heating $K_2HPO_4$, $Ba(NO_3)_2$, and $H_3PO_4$, the potassium and barium are present, in another embodiment, in a molar ratio, K:Ba, between about 2:3 to about 1:1.

In one embodiment, the catalyst can include an inert support that is constructed of a material comprising silicates, aluminates, carbons, metal oxides, and mixtures thereof. Alternatively, the carrier is inert relative to the reaction mixture expected to contact the catalyst. In another embodiment, the method of preparing the catalyst can further include mixing an inert support with the catalyst before, during, or after the mixing and heating of the phosphorus containing compounds, wherein the inert support includes silicates, aluminates, carbons, metal oxides, and mixtures thereof. In yet another embodiment, the method of preparing the catalyst can further include mixing an inert support with the catalyst before, during, or after the mixing and heating of the phosphorus containing compounds and the non-phosphorus containing compounds, wherein the inert support includes silicates, aluminates, carbons, metal oxides, and mixtures thereof.

Mixing of the phosphorus containing compounds or the phosphorus containing and non-phosphorus containing compounds of the catalyst can be performed by any method known to those skilled in the art, such as, by way of example and not limitation: solid mixing and co-precipitation. In the solid mixing method, the various components are physically mixed together with optional grinding using any method known to those skilled in the art, such as, by way of example and not limitation, shear, extensional, kneading, extrusion, and others. In the co-precipitation method, an aqueous solution or suspension of the various components, including one or more of the phosphate compounds, is prepared, followed by optional filtration and heating to remove solvents and volatile materials (e.g., water, nitric acid, carbon dioxide, ammonia, or acetic acid). The heating is typically done using any method known to those skilled in the art, such as, by way of example and not limitation, convection, conduction, radiation, microwave heating, and others.

In one embodiment of the invention, the catalyst is calcined. Calcination is a process that allows chemical reaction and/or thermal decomposition and/or phase transition and/or removal of volatile materials. The calcination process is carried out with any equipment known to those skilled in the art, such as, by way of example and not limitation, furnaces or reactors of various designs, including shaft furnaces, rotary kilns, hearth furnaces, and fluidized bed reactors. The calcination temperature is, in one embodiment, about 200° C. to about 1200° C.; in another embodiment, the calcination temperature is about 250° C. to about 900° C.; and in yet another embodiment, the calcination temperature is about 300° C. to 600° C. The calcination time is, in one embodiment, about one hour to about seventy-two hours.

While many methods and machines are known to those skilled in the art for fractionating particles into discreet sizes and determining particle size distribution, sieving is one of the easiest, least expensive, and common ways. An alternative way to determine the size distribution of particles is with light scattering. Following calcination, the catalyst is, in one embodiment, ground and sieved to provide a more uniform product. The particle size distribution of the catalyst particles includes a particle span that, in one embodiment, is less than about 3; in another embodiment, the particle size distribution of the catalyst particles includes a particle span that is less than about 2; and in yet another embodiment, the particle size distribution of the catalyst particles includes a particle span that is less than about 1.5. In another embodiment of the invention, the catalyst is sieved to a median particle size of about 50 μm to about 500 μm. In another embodiment of the invention, the catalyst is sieved to a median particle size of about 100 μm to about 200 μm.

In another embodiment, the catalyst is prepared by the following steps, which comprise: (a) combining a phosphorus containing compound, a nitrate salt, phosphoric acid, and water to form a wet mixture, wherein the molar ratio between phosphorus and the cations in both said phosphorus containing compound and said nitrate salt is about 1, (b) calcining said wet mixture stepwise at about 50° C., about 80° C., about 120° C., and about 450° C. to about 550° C. to produce a dried solid, and (c) grinding and sieving said dried solid to about 100 μm to about 200 μm, to produce said catalyst.

In another embodiment, the catalyst is prepared by the following steps, which comprise: (a) combining $MnPO_4 \cdot qH_2O$, $KNO_3$, and $H_3PO_4$, in a molar ratio of about 0.3:1:1, on an anhydrous basis, and water to give a wet mixture, (b) calcining said wet mixture stepwise at about 50° C., about 80° C., about 120° C., and about 450° C. to about 550° C. to give a dried solid, and (c) grinding and sieving said dried solid to about 100 μm to about 200 μm, to produce said catalyst.

In another embodiment, the catalyst is prepared by the following steps, which comprise: (a) combining $Ca_2P_2O_7$, $KNO_3$, and $H_3PO_4$, in a molar ratio of about 1.6:1:1, and water to give a wet mixture, (b) calcining said wet mixture stepwise at about 50° C., about 80° C., about 120° C., and about 450° C. to about 550° C. to give a dried solid, and (c) grinding and sieving said dried solid to about 100 μm to about 200 μm, to produce said catalyst.

In another embodiment, the catalyst is prepared by the following steps, which comprise: (a) combining a phosphorus containing compound, a nitrate salt, phosphoric acid, and water to give a wet mixture, wherein the molar ratio between phosphorus and the cations in both the phosphorus containing compound and nitrate salt is about 1, (b) heating said wet mixture to about 80° C. with stirring until near dryness to form a wet solid, (c) calcining said wet solid stepwise at about 50° C., about 80° C., about 120° C., and about 450° C. to about 550° C. to give a dried solid, and (d) grinding and sieving said dried solid to about 100 μm to about 200 μm, to produce said catalyst.

In another embodiment, the catalyst is prepared by the following steps, which comprise: (a) combining $Ba(NO_3)_2$, $K_2HPO_4$, and $H_3PO_4$, in a molar ratio of about 3:1:4, and water to give a wet mixture, (b) heating said wet mixture to about 80° C. with stirring until near dryness to form a wet solid, (c) calcining said wet solid stepwise at about 50° C., about 80° C., about 120° C., and about 450° C. to about 550° C. to give a dried solid, and (d) grinding and sieving said dried solid to about 100 μm to about 200 μm, to produce said catalyst.

In another embodiment, the catalyst is prepared by the following steps, which comprise: (a) combining $Mn(NO_3)_2 \cdot 4H_2O$, $K_2HPO_4$, and $H_3PO_4$, in a molar ratio of about 1:1.5:2, and water to give a wet mixture, (b) heating said wet mixture to about 80° C. with stirring until near dryness to form a wet solid, (c) calcining said wet solid stepwise at about 50° C., about 80° C., about 120° C., and about 450° C. to about 550° C. to give a dried solid, and (d) grinding and sieving said dried solid to about 100 μm to about 200 μm, to produce said catalyst.

In another embodiment, the catalyst is prepared by the following steps, which comprise: (a) combining $Ca_2P_2O_7$ and $KH_2PO_4$ in a molar ratio of about 3:1 to give a solid mixture, and (b) calcining said solid mixture stepwise at about 50° C., about 80° C., about 120° C., and about 450° C. to about 550° C., to produce said catalyst.

Following calcination and optional grinding and sieving, the catalyst can be utilized to catalyze several chemical reactions. Non-limiting examples of reactions are: dehydration of hydroxypropionic acid to acrylic acid (as described in further detail below), dehydration of glycerin to acrolein, dehydration of aliphatic alcohols to alkenes or olefins, dehydrogenation of aliphatic alcohols to ethers, other dehydrogenations, hydrolyses, alkylations, dealkylations, oxidations, disproportionations, esterifications, cyclizations, isomerizations, condensations, aromatizations, polymerizations, and other reactions that may be apparent to those having ordinary skill in the art.

IV. Methods of Producing Acrylic Acid, Acrylic Acid Derivatives, or Mixtures Thereof A method for dehydrating hydroxypropionic acid, hydroxypropionic acid derivatives, or mixtures thereof to acrylic acid, acrylic acid derivatives, or mixtures thereof is provided. The method includes contacting a stream comprising hydroxypropionic acid, hydroxypropionic acid derivatives, or mixtures thereof containing with a catalyst comprising: (a) at least one condensed phosphate anion selected from the group consisting of formulae (I), (II), and (III), $$[P_nO_{3n+1}]^{(n+2)-} \quad \text{(I)}$$

$$[P_nO_{3n}]^{n-} \quad \text{(II)}$$

$$[P_{(2m+n)}O_{(5m+3n)}]^{n-} \quad \text{(III)}$$

wherein n is at least 2 and m is at least 1, and (b) at least two different cations, wherein the catalyst is essentially neutrally charged, and further, wherein the molar ratio of phosphorus to the at least two different cations is between about 0.7 and about 1.7, whereby acrylic acid, acrylic acid derivatives, or mixtures thereof are produced as a result of said stream being contacted with the catalyst.

Alternative catalysts comprising anions selected from the group consisting of non-phosphorus containing anions, heteropolyanions, and phosphate adducts, and at least two different cations, wherein the catalyst is essentially neutrally charged, can be utilized for dehydrating hydroxypropionic acid, hydroxypropionic acid derivatives, or mixtures thereof to acrylic acid, acrylic acid derivatives, or mixtures thereof. Non-limiting examples of non-phosphorus containing anions are arsenates, condensed arsenates, nitrates, sulfates, vanadates, niobates, tantalates, selenates, and others that may be apparent to those having ordinary skill in the art. Non-limiting examples of heteropolyanions are heteropolyphosphates, such as arsenatophosphates, phosphoaluminates, phosphoborates, phosphocromates, phosphomolybdates, phosphosilicates, phosphosulfates, phosphotungstates, and others that may be apparent to those having ordinary skill in the art. Non-limiting examples of phosphate adducts are adducts of phosphate anions with telluric acid, halides, borates, carbonates, nitrates, sulfates, chromates, silicates, oxalates, mixtures thereof, or others that may be apparent to those having ordinary skill in the art.

Hydroxypropionic acid can be 3-hydroxypropionic acid, 2-hydroxypropionic acid (also called, lactic acid), 2-methyl hydroxypropionic acid, or mixtures thereof. Derivatives of hydroxypropionic acid can be metal or ammonium salts of hydroxypropionic acid, alkyl esters of hydroxypropionic acid, alkyl esters of 2-methyl hydroxypropionic acid, cyclic di-esters of hydroxypropionic acid, hydroxypropionic acid anhydride, or a mixture thereof. Non-limiting examples of metal salts of hydroxypropionic acid are sodium hydroxypropionate, potassium hydroxypropionate, and calcium hydroxypropionate. Non-limiting examples of alkyl esters of hydroxypropionic acid are methyl hydroxypropionate, ethyl hydroxypropionate, butyl hydroxypropionate, 2-ethylhexyl hydroxypropionate, or mixtures thereof. A non-limiting example of cyclic di-esters of hydroxypropionic acid is dilactide.

In one embodiment, the hydroxypropionic acid is lactic acid or 2-methyl lactic acid. In another embodiment, the hydroxypropionic acid is lactic acid. Lactic acid can be L-lactic acid, D-lactic acid, or mixtures thereof.

The acrylic acid derivatives can be acrylic acid oligomers, metal or ammonium salts of monomeric acrylic acid, metal or ammonium salts of acrylic acid oligomers, or mixtures thereof. Non-limiting examples of metal salts of acrylic acid are sodium acrylate, potassium acrylate, and calcium acrylate. Non-limiting examples of alkyl esters of acrylic acid are methyl lactate, ethyl lactate, or mixtures thereof.

The stream comprising hydroxypropionic acid, hydroxypropionic acid derivatives, or mixtures thereof can include a liquid stream and an inert gas (i.e., a gas otherwise inert to the reaction mixture under the conditions of the method) that can be separately or jointly fed into an evaporation vessel upstream of the catalyst reactor for the stream to become gaseous.

The liquid stream can include the hydroxypropionic acid, hydroxypropionic acid derivatives, or mixtures thereof and a diluent. Non-limiting examples of the diluent are water, methanol, ethanol, acetone, C3 to C8 linear and branched alcohols, C5 to C8 linear and branched alkanes, ethyl acetate, non-volatile ethers (including diphenyl ether), and mixtures thereof. In one embodiment, the diluent is water.

In certain embodiments, the liquid stream comprises an aqueous solution of lactic acid or lactic acid derivatives selected from the group consisting of lactide, lactic acid oligomers, salts of lactic acid, and alkyl lactates. In one embodiment, the liquid stream includes from about 2 wt % to about 95 wt % lactic acid or lactic acid derivatives, based on the total weight of the liquid stream. In another embodiment, the liquid steam includes from about 5 wt % to about 50 wt % lactic acid or lactic acid derivatives, based on the total weight of the liquid stream. In another embodiment, the liquid stream includes from about 10 wt % to about 25 wt % lactic acid or lactic acid derivatives, based on the total weight of the liquid stream. In another embodiment, the liquid stream includes about 20 wt % lactic acid or lactic acid derivatives, based on the total weight of the liquid stream. In another embodiment, the liquid stream comprises an aqueous solution of lactic acid along with derivatives of lactic acid. In another embodiment, the liquid stream comprises less than about 30 wt % of lactic acid derivatives, based on the total weight of the liquid stream. In another embodiment, the liquid stream comprises less than about 10 wt % of lactic acid derivatives, based on the total weight of the liquid stream. In yet another embodiment, the liquid stream comprises less than about 5 wt % of lactic acid derivatives, based on the total weight of the liquid stream.

The inert gas is a gas that is otherwise inert to the reaction mixture under the conditions of the method. Non-limiting examples of the inert gas are air, nitrogen, helium, argon, carbon dioxide, carbon monoxide, steam, and mixtures thereof. In one embodiment, the inert gas is nitrogen.

The stream comprising hydroxypropionic acid, hydroxypropionic acid derivatives, or mixtures thereof can be in the form of a gaseous mixture when contacting the catalyst. In one embodiment, the concentration of hydroxypropionic acid, hydroxypropionic acid derivatives, or mixtures thereof based on the total moles of said stream (calculated under STP conditions) is from about 0.5 mol % to about 50 mol %. In another embodiment, the concentration of hydroxypropionic acid, hydroxypropionic acid derivatives, or mixtures thereof based on the total moles of said stream (calculated under STP conditions) is from about 1 mol % to about 10 mol %. In another embodiment, the concentration of hydroxypropionic acid, hydroxypropionic acid derivatives, or mixtures thereof based on the total moles of said stream (calculated under STP conditions) is between about 1.5 mol % to about 3.5 mol %. In yet another embodiment, the concentration of hydroxypropionic acid, hydroxypropionic acid derivatives, or mixtures thereof based on the total moles of said stream (calculated under STP conditions) is about 2.5 mol %.

In one embodiment, the temperature at which said stream comprising hydroxypropionic acid, hydroxypropionic acid derivatives, or mixtures thereof contacts the catalyst is between about 120° C. and about 700° C. In another embodiment, the temperature at which said stream comprising hydroxypropionic acid, hydroxypropionic acid derivatives, or mixtures thereof contacts the catalyst is between about 150° C. and about 500° C. In another embodiment, the temperature at which said stream comprising hydroxypropionic acid, hydroxypropionic acid derivatives, or mixtures thereof contacts the catalyst is between about 300° C. and about 450° C. In yet another embodiment, the temperature at which said stream comprising hydroxypropionic acid, hydroxypropionic acid derivatives, or mixtures thereof contacts the catalyst is between about 325° C. and about 400° C.

In one embodiment, the stream comprising hydroxypropionic acid, hydroxypropionic acid derivatives, or mixtures thereof contacts the catalyst at a GHSV between about 720 h$^{-1}$ and about 36,000 h$^{-1}$. In another embodiment, the stream comprising hydroxypropionic acid, hydroxypropionic acid derivatives, or mixtures thereof contacts the catalyst at a GHSV between about 1,800 h$^{-1}$ to about 7,200 h$^{-1}$. In another embodiment, the stream comprising hydroxypropionic acid, hydroxypropionic acid derivatives, or mixtures thereof contacts the catalyst at a GHSV about 3,600 h$^{-1}$.

In one embodiment, the stream comprising hydroxypropionic acid, hydroxypropionic acid derivatives, or mixtures thereof contacts the catalyst at a pressure between about 0 psig and about 550 psig. In another embodiment, the stream comprising hydroxypropionic acid, hydroxypropionic acid derivatives, or mixtures thereof contacts the catalyst at a pressure of about 360 psig.

In one embodiment, the stream comprising hydroxypropionic acid, hydroxypropionic acid derivatives, or mixtures thereof contacts the catalyst in a reactor having an interior surface comprising material selected from the group consisting of quartz, borosilicate glass, silicon, hastelloy, inconel, manufactured sapphire, stainless steel, and mixtures thereof. In another embodiment, the stream comprising hydroxypropionic acid, hydroxypropionic acid derivatives, or mixtures thereof contacts the catalyst in a reactor having an interior surface comprising material selected from the group consisting of quartz or borosilicate glass. In another embodiment, the stream comprising hydroxypropionic acid, hydroxypropionic acid derivatives, or mixtures thereof contacts the catalyst in a reactor having an interior surface comprising borosilicate glass.

In one embodiment, the method includes contacting the catalyst with a gaseous mixture comprising hydroxypropionic acid, hydroxypropionic acid derivatives, or mixtures thereof under conditions sufficient to produce acrylic acid, acrylic acid derivatives, or mixtures thereof in a yield of at least 50%. In another embodiment, the method includes contacting the catalyst with a gaseous mixture comprising hydroxypropionic acid, hydroxypropionic acid derivatives, or mixtures thereof under conditions are sufficient to produce acrylic acid, acrylic acid derivatives, or mixtures thereof in a yield of at least about 70%. In another embodiment, the method includes contacting the catalyst with a gaseous mixture comprising hydroxypropionic acid, hydroxypropionic acid derivatives, or mixtures thereof under conditions are sufficient to produce acrylic acid, acrylic acid derivatives, or mixtures thereof in a yield of at least about 80%.

In another embodiment, the method conditions are sufficient to produce acrylic acid, acrylic acid derivatives, or mixtures thereof with a selectivity of at least about 50%. In another embodiment, the method conditions are sufficient to produce acrylic acid, acrylic acid derivatives, or mixtures thereof with a selectivity of at least about 70%. In another embodiment, the method conditions are sufficient to produce acrylic acid, acrylic acid derivatives, or mixtures thereof with a selectivity of at least about 80%.

In another embodiment, the method conditions are sufficient to produce acrylic acid, acrylic acid derivatives, or mixtures thereof with propanoic acid as an impurity, wherein the propanoic acid selectivity is less than about 5%. In another embodiment, the method conditions are sufficient to produce acrylic acid, acrylic acid derivatives, or mixtures thereof with propanoic acid as an impurity, wherein the propanoic acid selectivity is less than about 1%.

In another embodiment, the method conditions are sufficient to produce acrylic acid, acrylic acid derivatives, or mixtures thereof with a conversion of said hydroxypropionic acid, hydroxypropionic acid derivatives, or mixtures thereof of more than about 50%. In another embodiment, the method conditions are sufficient to produce acrylic acid, acrylic acid derivatives, or mixtures thereof with a conversion of said hydroxypropionic acid, hydroxypropionic acid derivatives, or mixtures thereof of more than about 80%.

Among the benefits attainable by the foregoing embodiments is the low yield of side products. In one embodiment, the conditions are sufficient to produce propionic acid in a yield of less than about 6% from lactic acid present in the gaseous mixture. In another embodiment, the conditions are sufficient to produce propionic acid in a yield of less than about 1%, from lactic acid present in the gaseous mixture In one embodiment, the conditions are sufficient to produce each of acetic acid, pyruvic acid, 1,2-propanediol, and 2,3-pentanedione in a yield of less than about 2% from lactic acid present in the gaseous stream. In another embodiment, the conditions are sufficient to produce each of acetic acid, pyruvic acid, 1,2-propanediol, and 2,3-pentanedione in a yield of less than about 0.5%, from lactic acid present in the gaseous stream. In one embodiment, the conditions are sufficient to produce acetaldehyde in a yield of less than about 8% from lactic acid present in the gaseous mixture. In another embodiment, the conditions are sufficient to produce acetaldehyde in a yield of less than about 4% from lactic acid present in the gaseous mixture. In another embodiment, the conditions are sufficient to produce acetaldehyde in a yield of less than about 3%, from lactic acid present in the gaseous mixture. These yields are believed to be, heretofore, unattainably low. Yet, these benefits are indeed achievable as further evidenced in the Examples set out below.

In one embodiment of the present invention, a method of making acrylic acid includes contacting: (a) a gaseous stream comprising: (i) lactic acid, (ii) water, and (iii) nitrogen, wherein said lactic acid is present in an amount of about 2.5 mol % and wherein said water is present in an amount of about 50 mol % based on the total moles of said gaseous stream, with (b) a catalyst comprising (i) $Ba_{2-x-s}K_{2x}H_{2s}P_2O_7$, and (ii) $(KPO_3)_n$, wherein x and s are greater or equal to 0 and less than about 0.5 and n is a positive integer, wherein, said contacting of said gaseous stream with said catalyst is performed at a temperature of about 300° C. to about 450° C., at a Gas Hourly Space Velocity (GHSV) of about 3,600 $h^{-1}$ and at a pressure of about 360 psig, in a reactor having an interior surface comprising material selected from the group consisting of quartz and borosilicate glass, whereby acrylic acid is produced as a result of said lactic acid being contacted with said catalyst.

In another embodiment of the present invention, a method of making acrylic acid includes contacting: (a) a gaseous stream comprising: (i) lactic acid, (ii) water, and (iii) nitrogen, wherein said lactic acid is present in an amount of about 2.5 mol % and wherein said water is present in an amount of 50 mol % based on the total moles of said gaseous stream, with (b) a catalyst prepared by a method comprising the following steps: (i) combining a phosphorus containing compound, a nitrate salt, phosphoric acid, and water to form a wet mixture, wherein the molar ratio between phosphorus and the cations in both said phosphorus containing compound and said nitrate salt is about 1; (ii) calcining said wet mixture stepwise at about 50° C., about 80° C., about 120° C., and about 450° C. to about 550° C. to produce a dried solid; and (iii) grinding and sieving said dried solid to about 100 μm to about 200 μm, to produce said catalyst, and wherein, said contacting of said gaseous stream with said catalyst is performed at a temperature of about 300° C. to about 450° C., at a GHSV of about 3,600 $h^{-1}$ and at a pressure of about 360 psig, in a reactor having an interior surface comprising material selected from the group consisting of quartz and borosilicate glass, whereby acrylic acid is produced as a result of said lactic acid being contacted with said catalyst.

In yet another embodiment of the present invention, a method of making acrylic acid includes contacting: (a) a gaseous stream comprising: (i) lactic acid, (ii) water, and (iii) nitrogen, wherein said lactic acid is present in an amount of about 2.5 mol % and wherein said water is present in an amount of about 50 mol % based on the total moles of said gaseous stream, with (b) a catalyst prepared by a method comprising the following steps: (i) combining $Ca_2P_2O_7$ and $KH_2PO_4$ in a molar ratio of about 3:1 to form a solid mixture; and (ii) calcining said solid mixture stepwise at about 50° C., about 80° C., about 120° C., and about 450° C. to about 550° C., to produce said catalyst; and wherein, said contacting of said gaseous stream with said catalyst is performed at a temperature of about 300° C. to about 450° C., at a GHSV of about 3,600 $h^{-1}$ and at a pressure of about 360 psig, in a reactor having an interior surface comprising material selected from the group consisting of quartz and borosilicate glass, whereby acrylic acid is produced as a result of said lactic acid being contacted with said catalyst.

A method for dehydrating glycerin to acrolein is provided. The method includes contacting a glycerin containing stream with a catalyst comprising: (a) at least one condensed phosphate anion selected from the group consisting of formulae (I), (II), and (III), $$[P_nO_{3n+1}]^{(n+2)-} \quad (I)$$

$$[P_nO_{3n}]^{n-} \quad (II)$$

$$[P_{(2m+n)}O_{(5m+3n)}]^{n-} \quad (III)$$

wherein n is at least 2 and m is at least 1, and (b) at least two different cations, wherein the catalyst is essentially neutrally charged, and further, wherein the molar ratio of phosphorus to the at least two different cations is between about 0.7 and about 1.7, whereby acrolein is produced as a result of said glycerin being contacted with the catalyst. Acrolein is an intermediate which can be converted to acrylic acid using conditions similar to what are used today in the second oxidation step in the propylene to acrylic acid process.

V Examples

The following examples are provided to illustrate the invention, but are not intended to limit the scope thereof. Examples 1 through 7 describe the preparation of different mixed condensed phosphate catalysts in accordance with various embodiments described above. Examples 8 through 12 describe the preparation of catalysts not according to the invention.

Example 1

An aqueous solution of barium nitrate, Ba(NO$_3$)$_2$ (85.36 mL of a 0.08 g/mL stock solution, 26 mmol, 99.999%; Sigma-Aldrich Co., St. Louis, Mo.; catalog #202754), was added to solid dibasic potassium phosphate, K$_2$HPO$_4$ (1.52 g, 8.7 mmol, ≥98%; Sigma-Aldrich Co., St. Louis, Mo.; catalog #P3786) at room temperature. Phosphoric acid, H$_3$PO$_4$ (2.45 mL of an 85 wt %, density=1.684 g/mL, 36 mmol; Acros Organics, Geel, Belgium; catalog #295700010), was added to the slurry, providing a solution containing potassium (K$^+$, M$^I$) and barium (Ba$^{2+}$, M$^{II}$), cations. The final pH of the suspension was 1.6. The acid-containing suspension was then dried slowly in a glass beaker at 80° C. using a heating plate while magnetically stirring the suspension until the liquid was evaporated and the material was almost completely dried. After evaporation, the material was transferred to a crushable ceramic. Heating was continued in a oven with air circulation (N30/80 HA; Nabertherm GmbH, Lilienthal, Germany) at 50° C. for 10 h, then at 80° C. for 10 h (0.5° C./min ramp), 120° C. for 2 hours (0.5° C./min ramp) to remove residual water followed by calcination at 450° C. for 4 hours (2° C./min ramp). After calcination, the material was left inside the oven until it cooled down by itself at a temperature below 100° C. before it was taken out of the oven. Finally, the catalyst was ground and sieved to about 100 µm to about 200 µm. The material was analyzed by X-ray diffraction (XRD) and energy dispersive spectroscopy coupled to scanning electron microscopy (EDS/SEM) allowing the identification of σ-Ba$_2$P$_2$O$_7$, α-Ba$_3$P$_4$O$_{13}$, Ba(NO$_3$)$_2$, and KPO$_3$ with some incorporation of K within the Ba-containing phases. The molar ratio between phosphorus (P) and the cations (M$^I$ and M$^{II}$) in the identified condensed phosphate salts was about 1 to about 1.3.

Example 2

Solid dibasic potassium phosphate, K$_2$HPO$_4$ (36.40 g, 209 mmol, ≥98%; Sigma-Aldrich Co., St. Louis, Mo.; catalog #P3786) was mixed quickly with an aqueous solution of barium nitrate, Ba(NO$_3$)$_2$ (2050 mL of a 0.08 g/mL stock solution, 627 mmol, 99.999%; Sigma-Aldrich Co., St. Louis, Mo.; catalog #202754) at room temperature. Phosphoric acid, H$_3$PO$_4$ (58.7 mL of an 85 wt %, density=1.684 g/mL, 857 mmol; Acros Organics, Geel, Belgium; catalog #295700010), was added to the slurry, providing a solution containing potassium (K$^+$, M$^I$) and barium (Ba$^{2+}$, M$^{II}$) cations. The final pH of the suspension was about 1.6. The acid-containing suspension was then dried slowly in a glass beaker at 80° C. using a heating plate while magnetically stirring the suspension until the liquid was evaporated and the material was almost completely dried. Heating was continued in a oven with air circulation (G1530A, HP6890 GC; Agilent Corp., Santa Clara, Calif.) at 50° C. for 5.3 h, then at 80° C. for 10 h (0.5° C./min ramp), following by cooling down at 25° C. The material was calcined at 120° C. for 2 hours (0.5° C./min ramp) followed by 450° C. for 4 hours (2° C./min ramp) using the same oven. After calcination, the material was left inside the oven until it cooled down by itself at a temperature below 25° C. before it was taken out of the oven. Finally, the catalyst was ground and sieved to about 100 µm to about 200 µm. The material was analyzed by XRD and EDS/SEM allowing the identification of σ-Ba$_2$P$_2$O$_7$, α-Ba$_3$P$_4$O$_{13}$, Ba(NO$_3$)$_2$, KPO$_3$, and some amorphous material with some incorporation of K within the Ba-containing phases. The molar ratio of phosphorus (P) to the cations (M$^I$ and M$^{II}$) in the identified condensed phosphate salts was about 1 to about 1.3.

Example 3

An aqueous solution of potassium nitrate, KNO$_3$ (1.51 mL of a 1 g/mL stock solution, 14.9 mmol, Sigma-Aldrich Co., St. Louis, Mo.; catalog #60415), was added to calcium diphosphate, Ca$_2$P$_2$O$_7$ (5.93 g, 23.3 mmol, Alfa Aesar, Ward Hill, Mass.; catalog #89836), at room temperature. Phosphoric acid, H$_3$PO$_4$ (1.05 mL of an 85 wt %, density=1.684 g/mL, 15.3 mmol, Acros Organics, Geel, Belgium; catalog #201140010), was added to the slurry, providing a suspension containing potassium (K$^+$, M$^I$) and calcium (Ca$^{2+}$, M$^{II}$) cations. The material was heated in a oven with air circulation (N30/80 HA; Nabertherm GmbH, Lilienthal, Germany) at 50° C. for 2 h, then at 80° C. for 10 h (0.5° C./min ramp), 120° C. for 2 hours (0.5° C./min ramp) to remove residual water followed by calcination at 450° C. for 4 hours (2° C./min ramp). After calcination, the material was left inside the oven until it cooled down by itself at a temperature below 100° C. before it was taken out of the oven. Finally, the catalyst was ground and sieved to about 100 µm to about 200 µm. The material was analyzed by XRD allowing the identification of β-Ca$_2$P$_2$O$_7$ and KPO$_3$. The molar ratio between phosphorus (P) and the cations (M$^I$ and M$^{II}$) in these condensed phosphate salts was about 1.

Example 4

Calcium diphosphate, Ca$_2$P$_2$O$_7$ (5.93 g, 23.3 mmol, Alfa Aesar, Ward Hill, Mass.; catalog #89836), and monobasic potassium monophosphate, KH$_2$PO$_4$ (1.08 g, 7.9 mmol, Sigma-Aldrich Co., St. Louis, Mo.; catalog #60216), which were previously sieved to about 100 µm to about 200 µm, were mixed in a glass bottle in a roller bench for 5 min, providing a solid mixture containing potassium (K$^+$, M$^I$) and calcium (Ca$^{2+}$, M$^{II}$) cations. The material was heated in a oven with air circulation (N30/80 HA; Nabertherm GmbH, Lilienthal, Germany) at 50° C. for 2 h, then at 80° C. for 10 h (0.5° C./min ramp), 120° C. for 2 hours (0.5° C./min ramp) to remove residual water followed by calcination at 550° C. for 4 hours (2° C./min ramp). After calcination, the material was left inside the oven until it cooled down by itself at a temperature below 100° C. before it was taken out of the oven. The material was analyzed by XRD allowing the identification of β-$Ca_2P_2O_7$ and $KPO_3$. The molar ratio between phosphorus (P) and the cations ($M^I$ and $M^{II}$) in these condensed phosphate salts was about 1.

Example 5

An aqueous solution of manganese (II) nitrate, Mn$(NO_3)_2$·$4H_2O$ (14.25 mL of a 0.3 g/mL stock solution, 17.0 mmol, Sigma-Aldrich Co., St. Louis, Mo.; catalog #63547), was added to dibasic potassium monophosphate, $K_2HPO_4$ (4.45 g, 25.5 mmol, Sigma-Aldrich Co., St. Louis, Mo.; catalog #P3786), at room temperature. Phosphoric acid, $H_3PO_4$ (2.39 mL of an 85 wt %, density=1.684 g/mL, 34.9 mmol, Acros Organics, Geel, Belgium; catalog #201140010), was added to the slurry, providing a suspension containing potassium ($K^+$, $M^I$) and manganese ($Mn^{2+}$, $M^{II}$) cations. The material was heated in a oven with air circulation (N30/80 HA; Nabertherm GmbH, Lilienthal, Germany) at 50° C. for 2 h, then at 80° C. for 10 h (0.5° C./min ramp), 120° C. for 2 hours (0.5° C./min ramp) to remove residual water followed by calcination at 450° C. for 4 hours (2° C./min ramp). After calcination, the material was left inside the oven until it cooled down by itself at a temperature below 100° C. before it was taken out of the oven. Finally, the catalyst was ground and sieved to about 100 μm to about 200 μm. The material was analyzed by XRD allowing the identification of $MnKP_2O_7$ and $KPO_3$; the molar ratio between phosphorus (P) and the cations ($M^I$ and $M^{II}$) in these condensed phosphate salts was about 1.

Example 6

An aqueous solution of potassium nitrate, $KNO_3$ (5.16 mL of a 1 g/mL stock solution, 51.1 mmol, Sigma-Aldrich Co., St. Louis, Mo.; catalog #60415), was added to manganese (III) phosphate, $MnPO_4$·$qH_2O$ (2.58 g, 17.2 mmol on an anhydrous basis, Alfa Aesar, Ward Hill, Mass.; catalog #A17868), at room temperature. Phosphoric acid, $H_3PO_4$ (3.58 mL of an 85 wt %, density=1.684 g/mL, 52.4 mmol, Acros Organics, Geel, Belgium; catalog #295700010), was added to the slurry, providing a suspension containing potassium ($K^+$, $M^I$) and manganase ($Mn^{3+}$, $M^{III}$) cations. The material was heated in a oven with air circulation (N30/80 HA; Nabertherm GmbH, Lilienthal, Germany) at 50° C. for 2 h, then at 80° C. for 10 h (0.5° C./min ramp), 120° C. for 2 hours (0.5° C./min ramp) to remove residual water followed by calcination at 550° C. for 4 hours (2° C./min ramp). After calcination, the material was left inside the oven until it cooled down by itself at a temperature below 100° C. before it was taken out of the oven. Finally, the catalyst was ground and sieved to about 100 μm to about 200 μm. The material was analyzed by XRD allowing the identification of $MnKP_2O_7$ and $KPO_3$. The molar ratio between phosphorus (P) and the cations ($M^I$ and $M^{II}$) in these condensed phosphate salts was about 1.

Example 7

Preparation of $Ba_3(PO_4)_2$

Sodium phosphate, $Na_3PO_4$ (85.68 g, 523 mmol, Sigma Aldrich Co., St. Louis, Mo.; catalog #342483), was dissolved in 580 mL of deionized water and the pH was adjusted to 7 with concentrated ammonium hydroxide. Barium nitrate, $Ba(NO_3)_2$ (121.07 g, 463 mmol, Sigma-Aldrich Co., St. Louis, Mo.; catalog #202754), was dissolved in 1220 mL of deionized water. The $Ba(NO_3)_2$ solution was added drop wise to the $Na_3PO_4$ solution while stirring and heating to 60° C., forming a white slurry during the addition. The pH was continuously monitored and concentrated ammonium hydroxide added dropwise to maintain pH 7. Heating and stirring at 60° C. continued for 60 min, at which time the solid was filtered and washed thoroughly with deionized water. The solid was suspended in 2 L of deionized water and filtered again and washed thoroughly with deionized water. In a vented oven, the filter cake was dried at 120° C. for 5 hours (1° C./min ramp), followed by calcination at 350° C. for 4 hours (2° C./min ramp) to give $Ba_3(PO_4)_2$ as a white solid.

Preparation of Catalyst:

An aqueous solution of potassium nitrate, $KNO_3$ (0.68 mL of a 1 g/mL stock solution, 6.8 mmol, Sigma-Aldrich Co., St. Louis, Mo.; catalog #60415), was added to barium phosphate, $Ba_3(PO_4)_2$ (4.07 g, 6.8 mmol) as prepared above, at room temperature. Copper (II) hydroxide phosphate, $Cu_2(OH)PO_4$ (3.23 g, 13.5 mmol, Sigma-Aldrich Co., St. Louis, Mo.; catalog #344400), and phosphoric acid, $H_3PO_4$ (0.47 mL of an 85 wt %, density=1.684 g/mL, 6.9 mmol, Acros Organics, Geel, Belgium; catalog #201140010), were added to the slurry, providing a suspension containing potassium ($K^+$, $M^I$), barium ($Ba^{2+}$, $M^{II}$), and copper ($Cu^{2+}$, $M^{II}$) cations. The material was heated in a oven with air circulation (N30/80 HA; Nabertherm GmbH, Lilienthal, Germany) at 50° C. for 2 h, then at 80° C. for 10 h (0.5° C./min ramp), 120° C. for 2 hours (0.5° C./min ramp) to remove residual water followed by calcination at 550° C. for 4 hours (2° C./min ramp). After calcination, the material was left inside the oven until it cooled down by itself at a temperature below 100° C. before it was taken out of the oven. The material was analyzed by XRD allowing the identification of α-$Ba_2P_2O_7$, $KPO_3$, and some amorphous material; the molar ratio between phosphorus (P) and the cations ($M^I$ and $M^{II}$) in these condensed phosphate salts was about 1.

Example 8 (Comparative)

A mixed condensed phosphate catalyst was prepared and used for comparative purposes. An aqueous solution of barium nitrate, $Ba(NO_3)_2$ (88.39 mL of a 0.08 g/mL stock solution, 27 mmol, 99.999%; Sigma-Aldrich Co., St. Louis, Mo.; catalog #202754), was added to solid dibasic potassium phosphate, $K_2HPO_4$ (1.57 g, 9.0 mmol, ≥98%; Sigma-Aldrich Co., St. Louis, Mo.; catalog #P3786) at room temperature. Phosphoric acid, $H_3PO_4$ (1.27 mL of an 85 wt %, density=1.684 g/mL, 19 mmol; Acros Organics, Geel, Belgium; catalog #295700010), was added to the slurry, providing a suspension containing potassium ($K^+$, $M^I$) and barium ($Ba^{2+}$, $M^{II}$) cations, such as the molar ratio between phosphorus (P) and the cations ($M^I$ and $M^{II}$) was about 0.6. The acid-containing slurry was then dried slowly in a glass beaker at 80° C. using a heating plate while stirring the suspension until the liquid was evaporated and the material was almost completely dried. After evaporation, the material was transferred to a crushable ceramic. Heating was continued in a oven with air circulation (N30/80 HA; Nabertherm GmbH, Lilienthal, Germany) at 50° C. for 2 h, then at 80° C. for 10 h (0.5° C./min ramp), 120° C. for 2 hours (0.5° C./min ramp) to remove residual water followed by calcination at 450° C. for 4 hours (2° C./min ramp). After calcination, the material was left inside the oven until it cooled down by itself at a temperature below 100° C. before it was taken out of the oven. Finally, the catalyst was ground and sieved to about 100 µm to about 200 µm.

Example 9 (Comparative)

A mixed condensed phosphate catalyst was prepared and used for comparative purposes. An aqueous solution of barium nitrate, $Ba(NO_3)_2$ (88.39 mL of a 0.08 g/mL stock solution, 27 mmol, 99.999%; Sigma-Aldrich Co., St Louis, Mo.; catalog #202754), was added to solid dibasic potassium phosphate, $K_2HPO_4$ (1.57 g, 9.0 mmol, ≥98%; Sigma-Aldrich Co., St Louis, Mo.; catalog #P3786) at room temperature. Phosphoric acid, $H_3PO_4$ (5.06 mL of an 85 wt %, density=1.684 g/mL, 74 mmol; Acros Organics, Geel, Belgium; catalog #295700010), was added to the slurry, providing a solution containing potassium ($K^+$, $M^I$) and barium ($Ba^{2+}$, $M^{II}$) cations, such as the molar ratio between phosphorus (P) and the cations ($M^I$ and $M^{II}$) was about 1.8. The acid-containing solution was then dried slowly in a glass beaker at 80° C. using a heating plate while stirring the suspension until the liquid was evaporated and the material was almost completely dried. After evaporation, the material was transferred to a crushable ceramic. Heating was continued in an oven with air circulation (N30/80 HA; Nabertherm GmbH, Lilienthal, Germany) at 50° C. for 2 h, then at 80° C. for 10 h (0.5° C./min ramp), 120° C. for 2 hours (0.5° C./min ramp) to remove residual water followed by calcination at 450° C. for 4 hours (2° C./min ramp). After calcination, the material was left inside the oven until it cooled down by itself at a temperature below 100° C. before it was taken out of the oven. Finally, the catalyst was ground and sieved to about 100 µm to about 200 µm.

Example 10 (Comparative)

A barium monophosphate catalyst, not according to the invention, was prepared and used for comparative purposes. Ammonium hydrogen phosphate, $(NH_4)_2HPO_4$ (142.20 g, 1.08 mol; Aldrich, St Louis, Mo.; catalog #215996), was dissolved in 1 L deionized water. Aqueous ammonium hydroxide, $NH_4OH$ (290 mL, 28-29%; EMD, Merck KGaA, Darmstadt, Germany; catalog #AX1303) was added slowly and heated gently until dissolved to form an ammonium phosphate solution. In a separate beaker, barium acetate, $(CH_3COO)_2Ba$ (285.43 g, 1.12 mol, Aldrich, St Louis, Mo.; catalog #243671), was dissolved in 1 L deionized water to form a barium acetate solution. The barium acetate solution was slowly added to the ammonium phosphate solution to form a white precipitate. After stirring for 45 min, the white solid was filtered. The solid was then re-suspended in 300 mL of deionized water, stirred for 10 min, and filtered again. This process was repeated two times. The resulting white solid was dried in a vented oven at 130° C. overnight. The solid was sieved to about 500 µm to 710 µm and calcined in a kiln at 500° C. for 4 hours (100° C./h ramp). After calcination, a sample of the catalyst was sieved to about 100 µm to about 200 µm. The material was analyzed by XRD allowing the identification of $Ba_3(PO_4)_2$.

Example 11 (Comparative)

A barium diphosphate catalyst, not according to the invention, was prepared and used for comparative purposes. A sample of dibasic barium phosphate, $BaHPO_4$ (Sigma-Aldrich Co., St. Louis, Mo.; catalog #31139), was calcined at 550° C. for 12 h, using a ceramic crucible and a temperature ramp of 2° C./min in a gravity convection oven. After calcination, the catalyst was ground using a mortar and a pestle and sieved to about 100 µm to about 200 µm. The material was analyzed by XRD allowing the identification of $\alpha\text{-}Ba_2P_2O_7$.

Example 12 (Comparative)

A barium tetraphosphate catalyst, not according to the invention, was prepared and used for comparative purposes. Dibasic barium monophosphate, $BaHPO_4$ (23.52 g, 100.8 mmol, Sigma-Aldrich Co., St Louis, Mo.; catalog #31139) and dibasic ammonium monophosphate, $(NH_4)_2HPO_4$ (4.44 g, 33.6 mmol, Sigma-Aldrich Co., St. Louis, Mo.; catalog #379980) were mixed and ground together using a mortar and pestle. The solid material was then calcined at 300° C. for 14 h, using a temperature ramp of 2° C./min in a gravity convection oven. After calcination, the catalyst was ground again using a mortar and a pestle, followed by calcination at 500° C. for 14 h using the same temperature ramp and oven as before. Finally, an additional round of grind and calcination at 750° C. for 14 h was performed. The catalyst was sieved to about 100 µm to about 200 µm. The material was analyzed by XRD allowing the identification of $\alpha\text{-}Ba_3P_4O_{13}$.

Example 13

An experiment was performed to determine the activity of a catalyst according to the present invention. Specifically, a catalyst prepared as described in Example 1 was subject to 21.6 hours of reaction time under the conditions set forth in Section VI. The results are reported in Table 2, below, wherein the acrylic acid yield and selectivity are corrected to TMB.

Example 14

Experiments were performed to consider the effect of the reactor material on the conversion of lactic acid to acrylic acid. All runs were performed using the same reactor configuration but only varying the conditions by using either a quartz-lined reactor or a 316 stainless steel (SS) reactor. No inert packing was used, the reactor temperature was maintained at 350° C., and the reactor was operated in each run at a GHSV of 3,438 $h^{-1}$. The results are reported in Table 3 below.

Example 15

Experiments without catalyst present further demonstrated the effect of feed stabilization in a quartz reactor. Empty reactors were compared to those packed with fused silica ($SiO_2$) (Sigma-Aldrich Co., St. Louis, Mo.) and Zirblast (Saint Gobain Zirpro, Le Pontet Cedex, France) in both stainless steel (SS) and quartz reactors. The results are reported in Table 4 below.

VI Test Procedures

XRD: The wide-angle data (WAXS) were collected on a STADI-P transmission mode diffractometer (Stoe & Cie GmbH, Darmstadt, Germany). The generator was operated at 40 kV/40 mA, powering a copper anode long-fine-focus Cu x-ray tube. The diffractometer incorporates an incident-beam curved germanium-crystal monochromator, standard incident-beam slit system, and an image plate-position sensitive detector with an angular range of about 124° 2θ. Data were collected in transmission mode. Samples were gently ground by hand using a mortar & pestle to fine powder consistency, if necessary, before loading into the standard sample holder for the instrument. Crystalline phases were identified using the most current powder diffraction database (from ICDD) using the Search/Match routines in Jade (Materials Data, Inc. v9.4.2).

SEM/EDS: The dry powders were dispersed onto a double sided copper or carbon tape which had been mounted onto a metal scanning electron microscope (SEM) substrate. Each specimen was coated with Au/Pd for approximately 65-80 s using a Gatan Alto 2500 Cryo preparation chamber. SEM imaging & energy dispersive spectroscopy (EDS) mapping were performed using either a Hitachi S-4700 FE-SEM or Hitachi S-5200 in-lens FE-SEM (Hitachi Ltd., Tokyo, Japan) both equipped for EDS with Bruker XFlash 30 mm2 SDD detectors (Quantax 2000 system with 5030 detector; Bruker Corp., Billerica, Mass.). EDS mapping was performed using an accelerating voltage of 10 kV in Analysis probe current mode. All maps were generated using Bruker Esprit V1.9 software within the Hypermap module.

Reactor—System A (0.2 mL scale reactor): Some of these conversions were carried out in a flow reactor system with a maximum catalyst bed volume of about 0.2 mL. The system comprised temperature and mass flow controllers and was supplied with separate liquid and gas feeds that were mixed together before reaching the catalyst bed. The gas feed was composed of molecular nitrogen ($N_2$) and helium (He), which was added as an internal standard for the gas chromatograph (GC) analysis. The liquid feed was an aqueous solution of lactic acid (20 wt % L-lactic acid) and was fed to the top of the reactor while controlling the pump pressure to about 360 psig to overcome any pressure drop from the catalyst bed. Quartz or stainless steel reactors with an aspect ratio (i.e., length/diameter) of 75 were used.

Various catalyst beds and gas feed flows were used resulting in a range of space velocities (reported in the Results section herein). The reactor effluent was also connected to another nitrogen dilution line, which diluted the effluent by a factor of two. The helium internal standard normalized any variation in this dilution for analytical purposes. The condensed products were collected by a liquid sampling system cooled to between 6.5° C. to 10° C. while the gaseous products accumulated on the overhead space of a collection vial. The overhead gaseous products were analyzed using sampling valves and online gas chromatography (GC).

The feed was equilibrated for 1 hour, after which time the liquid sample was collected for 2.7 hours and analyzed at the end of the experiment by offline HPLC. During this time, the gas products were analyzed online twice by GC and reported as an average. Liquid products were analyzed by high performance liquid chromatography (HPLC) using an Agilent 1200 Series instrument (Agilent Technologies, Santa Clara, Calif.), a Supelcogel-H column (4.6×250 mm; Supelco, St. Louis, Mo.), and a diode-array and a refraction index (RI) detectors. Analytes were eluted isocratically, using 0.005 M $H_2SO_4$ (aq.) as the elution buffer, over a period of 30 min and at a flow of 0.2 mL/min. The column and RI detector temperatures were set at 30° C. Gaseous products were analyzed by an Interscience Compact gas chromatography (GC) system (Interscience BV, Breda, Netherlands) using three detectors (one flame ionization detector—FID—and two thermal conductivity—TCD—detectors "A" and "B," referred to hereinafter as "TCD-A" and "TCD-B," respectively). The gaseous products were reported as an average given by two sequential GC chromatograms.

The TCD-A column was an Rt-Q Bond (Restek Corp., Bellefonte, Pa.), having 26 m in length and an I.D. of 0.32 mm with a film thickness of 10 μm and using a pre-column of 2 m. The pressure was set to 150 kPa, with a split flow of 10 mL/min. The column oven temperature was set to 100° C. with a vale oven temperature of 50° C. The flow was set to 5.0 mL/min, with a carrier gas of helium. The TCD-B column was a Mol sieve MSSA (Restek Corp., Bellefonte, Pa.), having a length of 21 m and a film thickness of 10 μm and using a pre-column of 2 m. The pressure was set to 200 kPa, with a split flow of 10 mL/min. The column oven temperature was set to 70° C. with a vale oven temperature of 50° C. The flow was set to 2.0 mL/min, with a carrier gas of argon. The FID column was a RTx-624 (Restek, Bellefonte, Pa.), having a length of 28 m and an inner diameter of 0.25 mm with a film thickness of 14 mm and using a pre-column of 2 m. The pressure was set to 100 kPa, with a split flow to 20 mL/min. The column oven temperature was set to 45° C. with a vale oven temperature of 50° C.

Reactor—System B (1.6 mL scale reactor): Some of these conversions were carried out in a packed bed flow reactor system with a catalyst bed volume of about 1.6 mL. A 13 inch (330 mm) long stainless steel glass lined tube (SGE Analytical Science Pty Ltd., Ringwood, Australia) with a 4.0 mm internal diameter (ID) was packed with glass wool (3 inch/76 mm bed length), topped by catalyst (1.6 $cm^3$ bed volume, 5 inch/127 mm bed length) to give an 2.55 $cm^3$ packed bed (8 inch/203 mm) and 1.6 $cm^3$ (5 inch/127 mm) of free space at the top of the reactor. The tube was placed inside an aluminum block and placed in a clam shell furnace series 3210 (Applied Test Systems, Butler, Pa.) such as the top of the packed bed was aligned with the top of the aluminum block. The reactor was set-up in a down-flow arrangement and was equipped with a Knauer Smartline 100 feed pump (Berlin, Germany), a Brooks 0254 gas flow controller (Hatfield, Pa.), a Brooks back pressure regulator, and a catch tank. The clam shell furnace was heated such that the reactor wall temperature was kept constant at about 350° C. during the course of the reaction. The reactor was supplied with separate liquid and gas feeds that were mixed together before reaching the catalyst bed. The gas feed was composed of molecular nitrogen ($N_2$) at about 360 psig and at a flow of 45 mL/min. The liquid feed was an aqueous solution of lactic acid (20 wt % L-lactic acid) and was fed at 0.045 mL/min (1.7 $h^{-1}$ LHSV), giving a residence time of about 1 s (3,600 $h^{-1}$ GHSV) at STP conditions. After flowing through the reactor, the gaseous stream was cooled and the liquids were collected in the catch tank for analysis by off-line HPLC using an Agilent 1100 system (Santa Clara, Calif.) equipped with a diode array detector (DAD) and a Waters Atlantis T3 column (Catalog #186003748; Milford, Mass.) using methods generally known by those having ordinary skill in the art. The gaseous stream was analyzed on-line by GC using an Agilent 7890 system (Santa Clara, Calif.) equipped with a FID detector and Varian CP-Para Bond Q column (Catalog #CP7351; Santa Clara, Calif.).

Reactor Feed: A solution (113.6 g) of biomass-derived lactic acid (88 wt %, Purac Corp., Lincolnshire, Ill.) was dissolved in distilled water (386.4 g) to provide a solution with an expected lactic acid concentration of 20 wt %. This solution was heated at 95° C. to 100° C. for 12-30 hours. The resulting mixture was cooled and analyzed by HPLC (described above) against known weight standards.

VII Results

Table 1 below, sets forth the parameters of the reactions with each catalyst that were carried out in the gas phase. When the 0.2 mL scale reactor was used, the reported yields were determined after 222 min (3 hours and 42 min) of reaction time and quartz reactors operating at 350° C. were employed. When the 1.6 mL scale reactor was used, a stainless steel glass lined reactor was employed and the reported yields were determined after about 150 min to about 650 min. The GHSV were as follows: 3,490 $h^{-1}$ in Example 1; 3,535 $h^{-1}$ in Examples 2, 10, 11, and 12; 3,414 $h^{-1}$ in Examples 3, 4, and 7; 3,566 $h^{-1}$ in Examples 5 and 6; and 3,379 $h^{-1}$ in Examples 8 and 9. In the table, "N.D." means that the value was not determined.

TABLE 1

| Example # | Reactor, (mL) | Molar Ratio R/cations, (—) | LA Conversion, (%) | AA Yield, (%) | AA Selectivity, (%) | AcH Yield, (%) | PA Yield, (%) | CO Yield, (%) | $CO_2$ Yield, (%) |
|---|---|---|---|---|---|---|---|---|---|
| 1 | 0.2 | 1-1.3 | 91 | 85 | 93 | 3 | 1 | 0 | 2 |
| 2 | 1.6 | 1-1.3 | 94 | 80 | 85 | 0 | N.D. | 3 | 1 |
| 3 | 0.2 | 1 | 78 | 68 | 86 | 0 | 0 | 1 | 0 |
| 4 | 0.2 | 1 | 72 | 54 | 76 | 12 | 0 | 1 | 1 |
| 5 | 0.2 | 1 | 74 | 61 | 82 | 4 | 0 | 0 | 2 |
| 6 | 0.2 | 1 | 49 | 41 | 85 | 5 | 0 | 0 | 2 |
| 7 | 0.2 | 1 | 82 | 52 | 63 | 17 | 0 | 1 | 3 |
| 8 | 0.2 | 0.6 | 100 | 0 | 0 | 7 | 1 | 0 | 12 |
| 9 | 0.2 | 1.8 | 78 | 29 | 37 | 35 | 0 | 3 | 1 |
| 10 | 1.6 | 0.7 | 32 | 5 | 17 | 0 | N.D. | 2 | 1 |
| 11 | 1.6 | 1 | 39 | 4 | 10 | 0 | N.D. | 6 | 0 |
| 12 | 1.6 | 1.3 | 99 | 2 | 2 | 2 | N.D. | 27 | 1 |

The results in Table 1 provide a convenient comparison of the conversion of lactic acid to acrylic acid using catalysts according to the invention (i.e., Examples 1 through 7) and those not according to the invention (i.e., Examples 8 through 12). Among other things, under the same or similar reaction conditions, catalysts according to the invention resulted in a far greater selectivity for acrylic acid and far lower selectivity for propionic acid than did those catalysts not according to the invention. Catalysts in Examples 8 and 9 had lower selectivities than the catalysts according to the invention, demonstrating that the presence of specific phosphate anions is important for high selectivity to acrylic acid. Catalysts in Examples 10, 11, and 12 had lower selectivity than the catalysts according to the invention, demonstrating that the presence of two different metals is important for high selectivity to acrylic acid. Furthermore, at lower molar ratios of phosphorus (P) to metals (i.e., comparative Example 8), decarboxylation (formation of $CO_2$) is favored, whereas at higher molar ratios (i.e., comparative Examples 9 and 12), decarbonylation (formation of CO) seems to be preferred.

TABLE 2

| | | | Selectivity | | | | |
|---|---|---|---|---|---|---|---|
| Run Time, (h) | LA Conversion, (%) | AA Yield, (%) | AA, (%) | Propionic Acid, (%) | Acetic Acid, (%) | AcH, (%) | $CO_2$, (%) |
| 2.7 | 75.2 | 66.3 | 88.2 | 0.0 | 0.9 | 5.7 | 1.6 |
| 5.4 | 69.7 | 65.2 | 93.5 | 0.0 | 0.0 | 6.1 | 0.0 |
| 21.6 | 64.5 | 57.6 | 89.4 | 0.0 | 2.4 | 6.9 | 0.0 |

The results in Table 2 show that the catalyst is stable for at least 21.6 hours insofar as the catalyst, over time, does not appear to significantly or detrimentally change relative to acrylic acid yield and selectivity and similarly does not appear to deteriorate relative to the selectivity for undesired by-products, such as propionic acid, acetic acid, acetaldehyde, and carbon dioxide.

TABLE 3

| Catalyst | Reactor Material | LA Conversion, (%) | AA Selectivity, (%) | AA Yield, (%) |
|---|---|---|---|---|
| Example 1 | SS | 90 | 64 | 58 |
| Example 1 | Quartz | 91 | 93 | 85 |

Although good yields were also observed using either quartz or stainless steel (SS), the data reported in Table 3 above, demonstrate that reactor composition may be important to feed stabilization and that quartz reactors performed better than the stainless steel ones in stabilizing the lactic acid feed from decomposition to side products, such as propionic acid, thus allowing for superior catalyst performance.

TABLE 4

| Inert Packing | Reactor Material | GHSV, ($h^{-1}$) | LA Conversion, (%) | AA Selectivity, (%) | AA Yield, (%) | PA Yield, (%) |
|---|---|---|---|---|---|---|
| Empty | Quartz | 3,453 | 18 | 0 | 0.2 | 0.2 |
| Empty | SS | 3,453 | 71.7 | 0 | 0.2 | 13.7 |
| Fused $SiO_2$ | Quartz | 3,489 | 25 | 0.05 | 1.4 | 2.9 |
| Fused $SiO_2$ | SS | 3,489 | 68.6 | 0 | 0 | 13.4 |
| Zirblast | Quartz | 3,489 | 21.8 | 0 | 0 | 0.2 |
| Zirblast | SS | 3,489 | 70 | 0 | 0 | 13 |

The results reported in Table 4 indicate that at high space velocities, very little byproducts were observed when quartz reactors, with or without inert packing, were used. Thus, it was determined that the use of quartz reactors minimized two important side reactions: lactic acid oligomerization and reduction to propionic acid. This is important to evaluating the true activity of catalysts.

The foregoing description is given for clearness of understanding only, and no unnecessary limitations should be understood therefrom, as modifications within the scope of the invention may be apparent to those having ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making acrylic acid, acrylic acid derivatives, or mixtures thereof comprising contacting a stream comprising hydroxypropionic acid, hydroxypropionic acid derivatives, or mixtures thereof with a catalyst comprising:
   (a) at least two different condensed phosphate anions selected from the group consisting of formulae (I) and (Ib),

   (I)

   (Ib)

wherein in formula I n is at least 2; and
   (b) at least two different cations,
   wherein the catalyst is essentially neutrally charged; and further, wherein the molar ratio of phosphorus to said at least two different cations is between about 0.7 and about 1.7, whereby acrylic acid, acrylic acid derivatives, or mixtures thereof are produced as a result of said stream being contacted with said catalyst,
   further, wherein said cations comprise:
   at least one monovalent cation; and
   at least one polyvalent cation.

2. The method of claim 1, wherein said stream further comprises:
   (a) diluent; and
   (b) inert gas selected from the group consisting of air, nitrogen, helium, argon, carbon dioxide, carbon monoxide, steam, and mixtures thereof.

3. The method of claim 2, wherein said stream is in the form of a gaseous mixture when contacting the catalyst.

4. The method of claim 3, wherein said diluent is water.

5. The method of claim 1, wherein said hydroxypropionic acid is lactic acid.

6. The method of claim 5, wherein the acrylic acid selectivity from said lactic acid is at least about 50%.

7. The method of claim 5, wherein the acrylic acid selectivity from said lactic acid is at least about 80%.

8. The method of claim 5, wherein the propionic acid selectivity from said lactic acid is less than about 5%.

9. The method of claim 5, wherein the propionic acid selectivity from said lactic acid is less than about 1%.

10. The method of claim 5, wherein the conversion of said lactic acid is more than about 50%.

11. The method of claim 5, wherein the conversion of said lactic acid is more than about 80%.

12. The method of claim 1, wherein said stream contacts said catalyst at a temperature of about 150° C. to about 500° C.

13. The method of claim 5, wherein said lactic acid contacts said catalyst at a temperature of about 300° C. to about 450° C.

14. The method of claim 3, wherein said hydroxypropionic acid, hydroxypropionic acid, or mixtures thereof are present in an amount between about 1 mol % and about 10 mol %, based on the total moles of said stream.

15. The method of claim 3, wherein said stream contacts said catalyst at a GHSV between about 720 $h^{-1}$ and about 36,000 $h^{-1}$.

16. The method of claim 15, wherein said stream contacts said catalyst at a GHSV of about 3,600 $h^{-1}$.

17. The method of claim 3, wherein said stream contacts said catalyst at a pressure between about 0 psig and about 550 psig.

18. The method of claim 3, wherein said stream contacts said catalyst at a pressure of about 360 psig.

19. The method of claim 1, wherein said stream is contacted with said catalyst in a reactor having an interior surface comprising material selected from the group consisting of quartz, borosilicate glass, silicon, hastelloy, inconel, manufactured sapphire, stainless steel, and mixtures thereof.

20. The method of claim 19, wherein said material is quartz or borosilicate glass.

21. The method of claim 1, wherein said monovalent cation is selected from the group consisting of $H^+$, $Li^+$, $Na^+$, $K^+$, $Rb^+$, $Cs^+$, and mixtures thereof.

22. The method of claim 1, wherein said polyvalent cation is selected from the group consisting of divalent cations, trivalent cations, tetravalent cations, pentavalent cations, and mixtures thereof.

23. The method of claim 22, wherein said polyvalent cation is selected from the group consisting of $Be^{2+}$, $Mg^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, $Zn^{2+}$, $Cd^{2+}$, $Sn^{2+}$, $Pb^{2+}$, $Ti^{3+}$, $Cr^{3+}$, $Mn^{3+}$, $Fe^{3+}$, $Al^{3+}$, $Ga^{3+}$, $Y^{3+}$, $In^{3+}$, $Sb^{3+}$, $Bi^{3+}$, $Si^{4+}$, $Ti^{4+}$, $Y^{4+}$, $Ge^{4+}$, $Mo^{4+}$, $Pt^{4+}$, $V^{5+}$, $Nb^{5+}$, $Sb^{5+}$, and mixtures thereof.

24. The method of claim 1, wherein said condensed phosphate anions are described by formulae (I) and (II).

25. The method of claim 24, wherein said catalyst comprises:
   (a) $Ba_{2-x-s}K_{2x}H_{2s}P_2O_7$ or $Ca_{2-x-s}K_{2x}H_{2s}P_2O_7$ or $Mn_{1-x-s}K_{1+3x}H_{3s}P_2O_7$ or $Mn_{1-x-s}K_{2+2x}H_{2s}P_2O_7$; and
   (b) $(KPO_3)_n$;
   wherein x and s are greater or equal to 0 and less than about 0.5 and n is a positive integer.

26. The method of claim 1, wherein the molar ratio of phosphorus to the cations in said catalyst is between about 0.8 and about 1.3.

27. The method of claim 1, wherein the molar ratio of phosphorus to the cations in said catalyst is about 1.

28. The method of claim 27, wherein said cations comprise:
   (a) $H^+$, $Li^+$, $Na^+$, $K^+$, $Rb^+$, $Cs^+$, and mixtures thereof; and
   (b) $Be^{2+}$, $Mg^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, $Zn^{2+}$, $Cd^{2+}$, $Sn^{2+}$, $Pb^{2+}$, $Ti^{3+}$, $Cr^{3+}$, $Mn^{3+}$, $Fe^{3+}$, $Al^{3+}$, $Ga^{3+}$, $Y^{3+}$, $In^{3+}$, $Sb^{3+}$, $Bi^{3+}$, $Si^{4+}$, $Ti^{4+}$, $V^{4+}$, $Ge^{4+}$, $Mo^{4+}$, $Pt^{4+}$, $V^{5+}$, $Nb^{5+}$, $Sb^{5+}$, and mixtures thereof.

29. The method of claim 1, wherein said catalyst includes an inert support that is constructed of a material comprising silicates, aluminates, carbons, metal oxides, and mixtures thereof.

* * * * *